US012622938B2

(12) United States Patent
Stamets

(10) Patent No.: US 12,622,938 B2
(45) Date of Patent: *May 12, 2026

(54) COMPOSITIONS AND METHODS FOR MODULATING INFLAMMATORY RESPONSE

(71) Applicant: TURTLE BEAR HOLDINGS, LLC, Shelton, WA (US)

(72) Inventor: Paul E. Stamets, Shelton, WA (US)

(73) Assignee: TURTLE BEAR HOLDINGS, LLC, Shelton, WA (US)

( * ) Notice: Subject to any disclaimer, the term of this patent is extended or adjusted under 35 U.S.C. 154(b) by 341 days.

This patent is subject to a terminal disclaimer.

(21) Appl. No.: 18/326,763

(22) Filed: May 31, 2023

(65) Prior Publication Data

US 2023/0364168 A1     Nov. 16, 2023

Related U.S. Application Data

(62) Division of application No. 17/221,437, filed on Apr. 2, 2021, now Pat. No. 11,730,784.

(60) Provisional application No. 63/029,830, filed on May 26, 2020, provisional application No. 63/004,788, filed on Apr. 3, 2020.

(51) Int. Cl.

| | |
|---|---|
| A61K 36/07 | (2006.01) |
| A61K 9/00 | (2006.01) |
| A61K 9/48 | (2006.01) |
| A61K 47/10 | (2017.01) |
| A61K 47/26 | (2006.01) |
| A61P 31/14 | (2006.01) |

(52) U.S. Cl.

CPC ............ *A61K 36/07* (2013.01); *A61K 9/0053* (2013.01); *A61K 9/48* (2013.01); *A61K 47/10* (2013.01); *A61K 47/26* (2013.01); *A61P 31/14* (2018.01); *A61K 2236/11* (2013.01); *A61K 2236/331* (2013.01)

(58) Field of Classification Search

CPC .................................................. A61K 36/074

See application file for complete search history.

(56) References Cited

U.S. PATENT DOCUMENTS

| | | |
|---|---|---|
| 7,790,175 B2 | 9/2010 | Eguchi et al. |
| 11,730,784 B2 | 8/2023 | Stamets |
| 11,779,620 B2 | 10/2023 | Stamets |
| 2009/0130138 A1 | 5/2009 | Stamets et al. |
| 2010/0047269 A1 | 2/2010 | Eguchi et al. |
| 2011/0189220 A1 | 8/2011 | Yang et al. |
| 2012/0294897 A1 | 11/2012 | Fiorentino Gomez et al. |
| 2014/0105928 A1 | 4/2014 | Stamets et al. |
| 2014/0364499 A1 | 12/2014 | Lau et al. |
| 2020/0023024 A1 | 1/2020 | Jin |
| 2021/0308200 A1 | 10/2021 | Stamets |
| 2021/0308201 A1 | 10/2021 | Stamets |

FOREIGN PATENT DOCUMENTS

| | | |
|---|---|---|
| CN | 102792851 A | 11/2012 |
| WO | 2016161138 A1 | 10/2016 |
| WO | 2020014745 A1 | 1/2020 |

OTHER PUBLICATIONS

European Search Report for Application No. 21782406.9, dated May 6, 2024 (11 pages).

European Search Report for Application No. 21779226.6, dated Mar. 1, 2024 (16 pages).

Hsieh, T.-C., et al. "Effects of extracts of Coriolus versicolor (I'm-Yunity™) on cell-cycle progression and expression of interleukins-$1\beta$,-6, and-8 in Promyelocytic HL-60 leukemic cells and mitogenically stimulated and nonstimulated human lymphocytes." The Journal of Alternative & Complementary Medicine 8.5 (2002): 591-602.

Ho, C. Y., et al. "Differential effect of Coriolus versicolor (Yunzhi) extract on cytokine production by murine lymphocytes in vitro." International immunopharmacology 4.12 (2004): 1549-1557.

Ascherl et al., "Infection With Human Immunodeficiency Virus-1 Increases Expression of Vascular Endothelial Cell Growth Factor in T Cells: Implications for Acquired Immunodeficiency Syndrome-Assicated Vasculopathy", Blood, vol. 93, No. 12, 1999, pp. 4323-4241.

Bachstetter et al., "The p38 MAP Kinase Family as Regulators of Proinflammatory Cytokine Production in Degenerative Diseases of CNS", Aging and Disease, vol. 1, No. 3, 2010, pp. 199-211.

Baig et al., "Evidence of the Covid-19 Virus Targeting the CNS: Tissue Distribution, Host-Virus Interaction, and Proposed Neurotropic Mechanisms", ACS Chemical Neuroscience, vol. 11, 2020, pp. 995-998.

Benson et al., "The mycelium of the *Trametes versicolor* (Turkey tail) mushroom and its fermented substrate each show potent and complementary immune activating properties in vitro", BMC Complementary and Alternative Medicine, vol. 19, 2019, 14 pages.

(Continued)

*Primary Examiner* — Terry A McKelvey

*Assistant Examiner* — Jacob B Boeckelman

(74) *Attorney, Agent, or Firm* — Michael Best & Friedrich LLP

(57)     ABSTRACT

Described herein are mushroom compositions and methods for treating, prophylaxis of, or ameliorating symptoms of one or more adverse reactions triggered by an infectious disease or condition that increases an anti-inflammatory response in a subject with such compositions. In one aspect the composition comprises an aqueous or solid fraction of a mycelium, a fermented substrate thereof, or a combination thereof optionally combined with one or more buffering agents, ethanol, and water.

19 Claims, 12 Drawing Sheets

Specification includes a Sequence Listing.

(56) References Cited

OTHER PUBLICATIONS

Chen et al., "Measuring IL-6 and sIL-6R in serum from patients treated with tocilizumb and/or siltuximab following CAR T cell therapy", J. Immunol. Meth., vol. 434, 2016, pp. 1-8.

Choi et al., "Antithrombotic and Antiplatelet Effects of Cordyceps militaris", Mycobiology, 2020, 5 pages.

Davis et al., "Differential Immune Activating, Anti-Inflammatory, and Regenerative Properties of the Aqueous, Ethanol, and Solid Fractions of a Medicinal Mushroom Blend", Journal of Inflammation Research, vol. 13, 2020, pp. 117-131.

De Lemos et al., "Neuroprotective Effects of the Absence of JNK1 or JNK3 Isoforms on Kainic Acid-Induced Temporal Lobe Epilepsy-Like Symptoms", Molecular Neurobiology, vol. 55, No. 5, 2018, pp. 4437-4452.

D'Elia et al., "Targeting the "Cytokine Storm" for Therapeutic Benefit", Clinical and Vaccine Immunology, vol. 20, No. 3, 2013, pp. 319-327.

Diao et al., "Reduction and Functional Exhaustion of T Cells in Patients with Coronavirus Disease", Frontiers in Immunology, vol. 11, 2020, pp. 1-8.

Fabian et al., "A small molecule-kinase interaction map for clinical kinase inhibitors", Nature Biotechnology, vol. 23, No. 3, 2005, pp. 329-336.

Gibbons et al., "Random Regression Models: A Comprehensive Approach to the Analysis of Longitudinal Psychiatric Data", Psychopharmacology Bulletin, vol. 24, No. 3, 1988, pp. 438-443.

Heagerty et al., "Time-Dependent ROC Curves for Censored Survival Data and a Diagnostic Marker", Biometrics, vol. 56, 2000, pp. 337-344.

Hedeker et al., "Random Regression Models for Multicenter Clinical Trials Data", Psychopharmacology Bulletin, vol. 27, No. 1, 1991, pp. 73-77.

International Search Report and Written Opinion for Application No. PCT/US21/25553 dated Aug. 6, 2021 (19 pages).

International Search Report and Written Opinion for Application No. PCT/US21/25564 dated Sep. 27, 2021 (18 pages).

Laird et al., "Random-Effects Models for Longitudinal Data", Biometrics, vol. 38, No. 4, 1982, pp. 963-974.

Liang et al., "The activation of BDNF reduced inflammation in a spinal cord injury model by TrkB/p38 Mark signaling", Experimental and Therapeutic Medicine, vol. 17, 2019, pp. 1688-1696.

Pleszczynska et al., "Fomitopsis betulina (formerly Piptoporus betulinus): the Iceman's polypore fungus with modern biotechnological potential", World J Microbiol Biotechnol, vol. 33, No. 83, 2017, 12 pages.

Prencipe et al., "Nerve Growth Factor Downregulates Inflammatory Response in Human Monocytes through TrkA", Journal of Immunology, vol. 192, No. 7, 2014, pp. 3345-3354.

Redondo-Castro et al., "Interleukin-1 primes human mesenchymal stem cells towards an anti-inflammatory and pro-trophic phenotype in vitro", Stem Cell Res. Ther., vol. 8, 2017, pp. 1-11.

Savory et al., "Viral Vascular Endothelial Growth Factor Plays a Critical Role in Orf Virus Infections", Journal of Virology, vol. 74, No. 20, 2000, pp. 10699-10706.

Thevarajan et al., "Breadth of concomitant immune responses prior to patient recovery: ac ase report of non-severe Covid-19", Nature Medicine, vol. 26, 2020, pp. 453-456.

Torkelson et al., "Phase 1 Clinical Trial of Trametes versicolor in Women with Breast Cancer", ISRN Oncology, 2012, pp. 1-7.

Velazquez-Salinas et al., "The Role of Interleukin 6 During Viral Infections", Frontiers in Microbiology, vol. 10, No. 1067, 2019, pp. 1-6.

Zheng et al., "Functional exhaustion of antiviral lymphocytes in Covid-19 patients", Cellular & Molecular Immunology, 2020, 3 pages.

Australian Patent Office. Examination Report No. 1 for Application No. 2021246099, dated Feb. 28, 2025 (3 pages).

Australian Patent Office. Examination Report No. 1 for Application No. 2021246519, dated Feb. 28, 2025 (3 pages).

Canada Patent Office Action for Application No. 3173635 dated Feb. 20, 2026 (8 pages).

FIG. 1

| Cytokine/ Chemokine Notes | Cytokine/ Chemokine | General Trends | | | Fold Change Approximations | | |
|---|---|---|---|---|---|---|---|
| | | FO PBS | FO EtOH | FO Pellet | FO PBS | FO EtOH | FO Pellet |
| Pro-Inflammatory | IFN-Gamma | ↑ | ↓ | ↑ | 700 | -50 | 800 |
| Pro-Inflammatory | IL-1B | ↑ | ↓ | ↑ | 12000 | - | 1500 |
| Pro-Inflammatory | IL-5 | ↑ | | ↑ | 300 | - | 200 |
| Pro-Inflammatory | IL-6 | ↑ | ↓ | ↑ | 100000 | - | 1500 |
| Pro-Inflammatory | IL-8 | ↑ | ↓ | ↑ | 7000 | - | 7000 |
| Pro-Inflammatory | IL-12p70 | ↑ | ↓ | ↑ | 300 | -50 | 250 |
| Pro-Inflammatory | IL-13 | ↑ | | ↑ | 300 | - | 200 |
| Pro-Inflammatory | IL-17A | ↑ | ↓ | ↑ | 800 | -75 | 800 |
| Pro-Inflammatory | Eotaxin | ↑ | ↓ | ↑ | 450 | -100 | 500 |
| Pro-Inflammatory | IP-10 | ↑ | ↓ | ↑ | 100 | -50 | 100 |
| Pro-Inflammatory | MCP-1 | ↑ | | ↑ | 11000 | - | 8000 |
| Pro-Inflammatory | MIP-1a | ↑ | ↓ | ↑ | 75000 | - | 140000 |
| Pro-Inflammatory | MIP-1B | ↑ | ↓ | ↑ | 8000 | - | 8000 |
| Pro-Inflammatory | RANTES | ↑ | ↓ | ↑ | 80 | -60 | 600 |
| Pro-Inflammatory | TNF-a | ↑ | ↓ | ↑ | 3000 | -50 | 5500 |
| | | | | | | | |
| Anti-Inflammatory | IL-1ra | ↑ | ↓ | ↑ | 1400 | -100 | 5000 |
| Anti-Inflammatory | IL-10 | ↑ | ↓ | | 400 | -50 | 200 |
| | | | | | | | |
| Pro- & Anti-Inflammatory | IL-2 | | ↓ | ↑ | 60 | -70 | 40 |
| Pro- & Anti-Inflammatory | IL-4 | ↑ | ↓ | ↑ | 550 | -50 | 600 |
| Pro- & Anti-Inflammatory | IL-7 | ↑ | ↓ | ↑ | 125 | -50 | 150 |
| Pro- & Anti-Inflammatory | IL-9 | ↑ | ↓ | ↑ | 1600 | -75 | 1700 |
| Pro- & Anti-Inflammatory | IL-15 | ↑ | ↓ | ↑ | 50 | -50 | 80 |

CD69 expression on CD56+ T lymphocytes products in PBS (Donor 1)

CD69 expression on NK cells products in PBS

CD69 expression on CD56+ T lymphocytes products in PBS

FIG. 8

| Cytokine/Chemokine Notes | Cytokine/Chemokine | General Trends | | Fold Change Approximation | | General Trends | | Fold Change Approximation | | General Trends | | Fold Change Approximation | |
|---|---|---|---|---|---|---|---|---|---|---|---|---|---|
| | | TV Mycelium PBS | TV Mycelium Pellet | TV Mycelium PBS | TV Mycelium Pellet | TV Fermented Substrate PBS | TV Fermented Substrate Pellet | TV Fermented Substrate PBS | TV Fermented Substrate Pellet | TV Blend PBS | TV Blend Pellet | TV Blend PBS | TV Blend Pellet |
| Pro-Inflammatory | IFN-Gamma | ↑ | ↑ | 1750 | 350 | ↑ | ↑ | 2000 | 3500 | ↑ | ↑ | 150 | 1400 |
| Pro-Inflammatory | IL-1B | ↑ | ↑ | 9500 | 2000 | ↑ | ↑ | 9500 | 9500 | ↑ | ↑ | 2500 | 16000 |
| Pro-Inflammatory | IL-5 | ↑ | | 200 | - | ↑ | ↑ | 250 | 1250 | ↑ | | 50 | 350 |
| Pro-Inflammatory | IL-6 | ↑ | ↑ | 14000 | 3000 | ↑ | ↑ | 8000 | 8000 | ↑ | ↑ | 8000 | 13000 |
| Pro-Inflammatory | IL-8 | ↑ | ↑ | 8500 | 2500 | ↑ | ↑ | 17500 | 17500 | ↑ | ↑ | 3250 | 7000 |
| Pro-Inflammatory | IL-12p70 | | | - | - | | ↑ | - | 140 | | ↑ | - | - |
| Pro-Inflammatory | IL-13 | | | - | - | | | - | - | | | - | - |
| Pro-Inflammatory | IL-17A | ↑ | ↑ | 950 | 300 | ↑ | ↑ | 1500 | 4000 | ↑ | ↑ | 300 | 1250 |
| Pro-Inflammatory | Eotaxin | ↑ | ↑ | 350 | 200 | ↑ | ↑ | 1200 | 1800 | ↑ | ↑ | 300 | 800 |
| Pro-Inflammatory | IP-10 | - | ↑ | 275 | 150 | ↑ | ↑ | 300 | 800 | | ↑ | - | 350 |
| Pro-Inflammatory | MCP-1 | ↑ | ↑ | 3500 | 700 | ↑ | ↑ | 6000 | 10000 | | ↑ | 300 | 4400 |
| Pro-Inflammatory | MIP-1a | | ↑ | 10000 | 18000 | | ↑ | 50000 | 29000 | | ↑ | 12000 | 30000 |
| Pro-Inflammatory | MIP-1B | ↑ | ↑ | 600 | 500 | ↑ | ↑ | 3500 | 6500 | ↑ | ↑ | 300 | 2200 |
| Pro-Inflammatory | RANTES | ↑ | ↑ | 250 | 250 | ↑ | ↑ | 100 | 140 | ↑ | ↑ | 175 | 275 |
| Pro-Inflammatory | TNF-a | ↑ | ↑ | 2000 | 1600 | ↑ | ↑ | 3500 | 11500 | ↑ | ↑ | 3500 | 6000 |
| | | | | | | | | | | | | | |
| Anti-Inflammatory | IL-1ra | ↑ | ↑ | 400 | 1250 | ↑ | ↑ | 1000 | 1000 | ↑ | | 250 | 1000 |
| Anti-Inflammatory | IL-10 | ↑ | ↑ | 100 | - | ↑ | ↑ | 100 | 800 | | | - | - |
| | | | | | | | | | | | | | |
| Pro- & Anti-Inflammatory | IL-2 | ↑ | ↑ | 300 | 250 | ↑ | ↑ | 700 | 2300 | ↑ | ↑ | 300 | 900 |
| Pro- & Anti-Inflammatory | IL-4 | ↑ | ↑ | 550 | 300 | ↑ | ↑ | 1100 | 2800 | ↑ | ↑ | 300 | 1100 |
| Pro- & Anti-Inflammatory | IL-7 | ↑ | | - | - | ↑ | ↑ | - | - | | ↑ | - | - |
| Pro- & Anti-Inflammatory | IL-9 | ↑ | ↑ | 150 | 125 | ↑ | ↑ | 200 | 225 | ↑ | ↑ | 100 | 175 |
| Pro- & Anti-Inflammatory | IL-15 | | | - | - | | ↑ | - | 400 | | | - | - |

Interaction of Fo and Inflammation-Related MAPKs

Interaction of the He-Fo and Inflammation-Related MAPKs

COMPOSITIONS AND METHODS FOR MODULATING INFLAMMATORY RESPONSE

CROSS-REFERENCE TO RELATED APPLICATIONS

This application is a divisional of U.S. patent application Ser. No. 17/221,437, filed on Apr. 2, 2021, which claims priority to U.S. Provisional Patent Application No. 63/004,788, filed on Apr. 3, 2020 and U.S. Provisional Patent Application No. 63/029,830, filed on May 26, 2020, the entire contents of each of which are fully incorporated herein by reference.

REFERENCE TO SEQUENCE LISTING

This application is filed with a Computer Readable Form of a Sequence Listing in accord with 37 C.F.R. § 1.821(c). The text file submitted by EFS, "888690-9006-US06_sequence_listing_30-MAY-2023_5 T25," was created on May 30, 2023, contains 13, sequences, has a file size of 11.0 Kbytes, and is hereby incorporated by reference in its entirety.

TECHNICAL FIELD

Described herein are mushroom compositions and methods for treating, prophylaxis of, or ameliorating symptoms of one or more adverse reactions triggered by an infectious disease or condition that increases an anti-inflammatory response in a subject with such compositions. In one aspect the composition comprises an aqueous or solid fraction of a mycelium, a fermented substrate thereof, or a combination thereof optionally combined with one or more buffering agents, ethanol, and water.

BACKGROUND

Cytokines are a broad group of small proteins involved in immunomodulatory cell signaling, including interleukins, interferons, and growth factors. These peptides are secreted by immune cells and cannot permeate the cell membrane; however, by interacting with their matching receptors on the cell's surface, cytokines trigger intracellular signaling cascades, altering gene expression and inducing an immune response. Several factors can influence a cytokine's effect, including peptide and/or receptor abundance, downstream signaling cascades, expression of genes and transcription factors, feedback loops, and complementary or competing interactions associated with other cytokines. Depending on their activity, cytokines may either be pro-inflammatory or anti-inflammatory, and may be associated with an acute or sustained response.

A healthy cellular immune response involves a pro-inflammatory reaction conferring immunological protection, delicately balanced by anti-inflammatory responses that protect host tissues from incurring damage. However, certain pathogens may upset this balance by inducing an overactive host immune response, leading to systemic expression of inflammatory cytokines called hypercytokinemia, or a "cytokine storm."

First applied to SARS-CoV-1, the term "cytokine storm" refers to an overproduction of inflammatory cytokines, resulting in an immune response that damages the body. Although cytokine storms can also be associated with non-infectious diseases, they are archetypically associated with severe lung infections. When a lower respiratory infection causes acute lung injury, local inflammatory cytokines can spread via the circulatory system, resulting in multiple organ failure and symptomatology akin to systemic sepsis syndrome.

In the case of COVID-19, the disease caused by SARS-CoV-2, critically ill patients often develop acute respiratory disease syndrome (ARDS) and display hyperinflammation consistent with a cytokine storm. When afflicted by ARDS, patients display elevated levels of proinflammatory cytokines TNF-α and IL-1β in the lungs. Consistent with other hyperinflammatory syndromes, several inflammatory markers are predictive of mortality in COVID-19 patients, including elevated ferritin, IL-2, IL-6, IL-7, and TNF-α. Analyses of patients infected with the related SARS-CoV-1 also found high levels of inflammatory cytokines (IL-1, IL-6, IL-12) and extremely low levels of the anti-inflammatory IL-10. However, studies of SARS-CoV-2 infected patients suggest that IL-10 levels may actually be directly correlated with COVID-19 severity. A retroactive analysis of 113 deceased patients with COVID-19 found elevated levels of IL-2, IL-6, IL-8, TNF-α, and IL-10 compared to those who recovered. Another study found that patients with severe SARS-CoV-2 seem to present with significantly elevated IL-2, IL-6 and IL-10 compared to febrile controls; of these three cytokines, IL-2 and IL-6 appear to be indicators of disease severity.

Various methods have been attempted to reduce inflammation in COVID-19 patients, ranging from steroids to acupuncture; however, the medical science community has not reached consensus regarding the impact that various anti-inflammatory agents can have on SARS-CoV-2 viral infection and/or COVID-19 disease development. In the case of SARS-CoV and MERS-CoV, corticosteroid treatment did not prove a beneficial therapy and actually impaired viral clearance, suggesting a need for alternative means of controlling dysregulated inflammation associated with a cytokine storm. Since immune dysregulation and induced cytokine storms are associated with disease severity and mortality, antiviral agents may prove insufficient for treatment of respiratory distress in late-stage disease development; targeted immunomodulation may also be required to mitigate the harmful effects of pulmonary inflammation.

The urgency of COVID-19 is clear. Despite multiple advances in modern medicine, traditional pharmacotherapy has limited available antiviral options for the treatment of COVID-19. While antiretroviral and antimalarial options are being explored, current treatment options are primarily limited to supportive care during the later stages of disease. Circumstances such as these demand that the search be broadened to outside of the available pharmacopeia.

Since immune dysregulation and induced cytokine storms are associated with disease severity and mortality, antiviral agents may prove insufficient for treatment of respiratory distress in late-stage disease development; targeted immunomodulation may also be required to mitigate the harmful effects of pulmonary inflammation. Thus, there remains a need for a novel therapeutic to combat COVID-19 by stimulating immune activity while concurrently modulating harmful inflammation.

SUMMARY

One embodiment described herein is a composition for treating, prophylaxis of, or ameliorating symptoms of one or more adverse reactions triggered by an infectious disease or condition that increases an anti-inflammatory response in a subject, the composition comprising: an aqueous or solid fraction of a mycelium, a fermented substrate thereof, or a combination thereof; one or more buffering agents; ethanol; and water. In one aspect, the mycelium comprises one or more of *Fomitopsis officinalis, Trametes versicolor, Hericium erinaceus,* or *Inonotus obliquus.* In another aspect, the mycelium is *Fomitopsis officinalis* mycelium. In another aspect, the aqueous or solid fraction comprises beta-glucans. In another aspect, the buffering agent comprises phosphate buffered saline. In another aspect, the composition comprises about 200 mg to about 10 g of *Trametes versicolor, Hericium erinaceus,* or *Inonotus obliquus* mycelium. In another aspect, the composition comprises about 200 mg to about 10 g of *Fomitopsis officinalis* mycelium. In another aspect, the composition further comprises one or more preservatives, flavorings, colorings, stabilizers, emulsifiers, or other pharmaceutically acceptable excipients. In another aspect, the infectious disease or condition increases expression of growth factors. In another aspect, the growth factors comprise one or more of basic fibroblast growth factor or vascular endothelial growth factor.

Another embodiment described herein is a composition for treating, prophylaxis of, or ameliorating symptoms of one or more adverse reactions triggered by an infectious disease or condition that increases an anti-inflammatory response in a subject, the composition comprising: an aqueous or solid fraction of *Fomitopsis officinalis* mycelium, a fermented substrate thereof, or a combination thereof; one or more buffering agents; ethanol; and water. In one aspect, the aqueous or solid fraction comprises beta-glucans. In another aspect, the buffering agent comprises phosphate buffered saline. In another aspect, the infectious disease or condition increases expression of growth factors. In another aspect, the growth factors comprise one or more of basic fibroblast growth factor or vascular endothelial growth factor. In another aspect, the composition comprises about 200 mg to about 10 g of *Fomitopsis officinalis* mycelium. In another aspect, the infectious disease comprises a bacterial infection. In another aspect, the bacterial infection comprises one or more of *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae,* or Non-tuberculosis *Mycobacterium.* In another aspect, the infectious disease comprises a viral infection. In another aspect, the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), or Herpesviridae (human herpes viruses, Varicella zoster virus, Epstein-Barr virus, cytomegalovirus). In another aspect, the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, OC43, or HKU1.

Another embodiment described herein is a composition comprising an aqueous or ethanolic extract of *Fomitopsis officinalis* mycelium.

Another embodiment described herein is a use of a composition described herein for modulating an inflammatory response comprising administering an effective amount of the composition to a subject in need thereof. In one aspect, the inflammatory response comprises release of anti-inflammatory and pro-inflammatory cytokines. In another aspect, the pro-inflammatory cytokines comprise one or more of interleukin-1β, interleukin-2, interleukin-4, interleukin-5, interleukin-6, interleukin-7, interleukin-8, interleukin-9, interleukin-12p70, interleukin-13, interleukin-15, interleukin-17A, tumor necrosis factor-α, interferon-γ, monocyte chemoattractant protein 1, eotaxin, interferon gamma-induced protein 10, granulocyte colony-stimulating factor, macrophage inflammatory protein 1α, macrophage inflammatory protein 1β, or RANTES. In another aspect, the anti-inflammatory cytokines comprise one or more of interleukin-1 receptor antagonist, interleukin-2, interleukin-4, interleukin-7, interleukin-9, interleukin-10, or interleukin-15.

Another embodiment described herein is a means for modulating an inflammatory response comprising administering to a subject in need thereof an effective amount of a composition described herein. In one aspect, the inflammatory response comprises release of anti-inflammatory and pro-inflammatory cytokines.

Another embodiment described herein is a method for treating, prophylaxis of, or ameliorating symptoms of an infectious disease comprising: administering to a subject in need thereof an effective amount of a composition comprising: an aqueous or solid fraction of a mycelium, a fermented substrate thereof, or a combination thereof; one or more buffering agents; ethanol; and water. In one aspect, the mycelium comprises one or more of *Fomitopsis officinalis, Trametes versicolor, Hericium erinaceus,* or *Inonotus obliquus.* In another aspect, the mycelium is *Fomitopsis officinalis* mycelium. In another aspect, the composition comprises about 200 mg to about 10 g of *Trametes versicolor, Hericium erinaceus,* or *Inonotus obliquus* mycelium. In another aspect, the composition comprises about 200 mg to about 10 g of *Fomitopsis officinalis* mycelium. In another aspect, the aqueous or solid fraction comprises beta-glucans. In another aspect, a dose of the composition is administered to the subject 3 times per day. In another aspect, the composition is in the form of a capsule. In another aspect, the dose comprises at least 4 capsules. In another aspect, the composition is administered to the subject for about 10 to 30 consecutive days. In another aspect, the composition is administered to the subject for about 14 days. In another aspect, the subject has COPD, Cardiovascular disease, diabetes mellitus, hypertension, or a combination thereof. In another aspect, the subject is at least 60 years old. In another aspect, the composition is administered orally. In another aspect, the composition further comprises one or more preservatives, flavorings, colorings, stabilizers, emulsifiers, or other pharmaceutically acceptable excipients. In another aspect, the infectious disease comprises one or more symptoms comprising shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure. In another aspect, the infectious disease comprises a bacterial infection. In another aspect, the bacterial infection comprises one or more of *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae,* or Non-tuberculosis *Mycobacterium.* In another aspect, the infectious disease comprises a viral infection. In another aspect, the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), or Herpesviridae (human herpes viruses, Varicella zoster virus, Epstein-Barr virus, cytomegalovirus). In another aspect, the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, 0043, or HKU1.

Another embodiment described herein is a method for treating, prophylaxis of, or ameliorating symptoms of a bacterial or viral infection comprising administering an effective amount of an aqueous or solid extract of one or more of *Fomitopsis officinalis, Trametes versicolor, Hericium erinaceus*, or *Inonotus obliquus*.

Another embodiment described herein is a method for modulating an inflammatory response associated with a bacterial or viral infection comprising administering an effective amount of an aqueous or solid extract of one or more of *Fomitopsis officinalis, Trametes versicolor, Hericium erinaceus*, or *Inonotus obliquus*. In one aspect, the administration modulates one or more of cytokine storms, neuroinflammation, or blood clotting.

Another embodiment described herein is a method of manufacturing a composition as described herein, the method comprising: growing a mushroom on a substrate; and, separating the mushroom mycelium from a fruitbody and the substrate. In one aspect, the method further comprises incubating the mycelium with a solvent, forming a solution; extracting an aqueous fraction from the solution; and extracting a solid fraction from the solution. In another aspect, the method further comprises freeze-drying the mycelium; and grinding the dried mycelium into a powder. In another aspect, a pressure of about 1,500 mbar to about 2,000 mbar is applied to the mycelium during freeze-drying. In another aspect, a temperature of about 75° C. to 95° C. is applied to the mycelium. In another aspect, the substrate comprises one or more of rice, oat, straw, or sawdust. In another aspect, the mushroom is grown on a substrate at about 15° C. to about 30° C. for about 20 to about 120 days. In another aspect, the mushroom is grown on a substrate at about 20° C. to about 25° C. for about 40 days. In another aspect, the solvent is cold water.

Another embodiment described herein is a method for treating or lessening the severity of any type of pain in a subject in need thereof comprising: administering to the subject an effective amount of a composition comprising: an aqueous or solid fraction of a mycelium, a fermented substrate thereof, or a combination thereof; one or more buffering agents; ethanol; and water. In one aspect, the mycelium comprises one or more of *Fomitopsis officinalis, Trametes versicolor, Hericium erinaceus*, or *Inonotus obliquus*. In another aspect, the mycelium is *Fomitopsis officinalis* mycelium. In another aspect, the composition comprises about 200 mg to about 10 g of *Trametes versicolor, Hericium erinaceus*, or *Inonotus obliquus* mycelium. In another aspect, the composition comprises about 200 mg to about 10 g of *Fomitopsis officinalis* mycelium. In another aspect, the aqueous or solid fraction comprises beta-glucans. In another aspect, a dose of the composition is administered to the subject 3 times per day. In another aspect, the composition is in the form of a capsule. In another aspect, the dose comprises at least 4 capsules. In another aspect, the composition is administered orally. In another aspect, the composition further comprises one or more preservatives, flavorings, colorings, stabilizers, emulsifiers, or other pharmaceutically acceptable excipients. In another aspect, the pain comprises one or more types of neuropathic pain, somatic pain, visceral pain, and other types of pain.

A method for enhancing a viral therapy comprising: administering to a subject an effective amount of a composition comprising: an aqueous or solid fraction of a mycelium, a fermented substrate thereof, or a combination thereof; one or more buffering agents; ethanol; and water. In one aspect, the viral therapy comprises a vaccine, an antiviral drug, or a combination thereof. In another aspect, the mycelium comprises one or more of *Fomitopsis officinalis, Trametes versicolor, Hericium erinaceus*, or *Inonotus obliquus*. In another aspect, the mycelium is *Fomitopsis officinalis* mycelium. In another aspect, the composition comprises about 200 mg to about 10 g of *Trametes versicolor, Hericium erinaceus*, or *Inonotus obliquus* mycelium. In another aspect, the composition comprises about 200 mg to about 10 g of *Fomitopsis officinalis* mycelium.

DESCRIPTION OF THE DRAWINGS

FIG. 1 shows the induction of pro- and anti-inflammatory cytokines and chemokines by FO fractions.

FIG. 8 shows the heatmap of general cytokine trends and approximate expression data.

DETAILED DESCRIPTION

Figure 2:
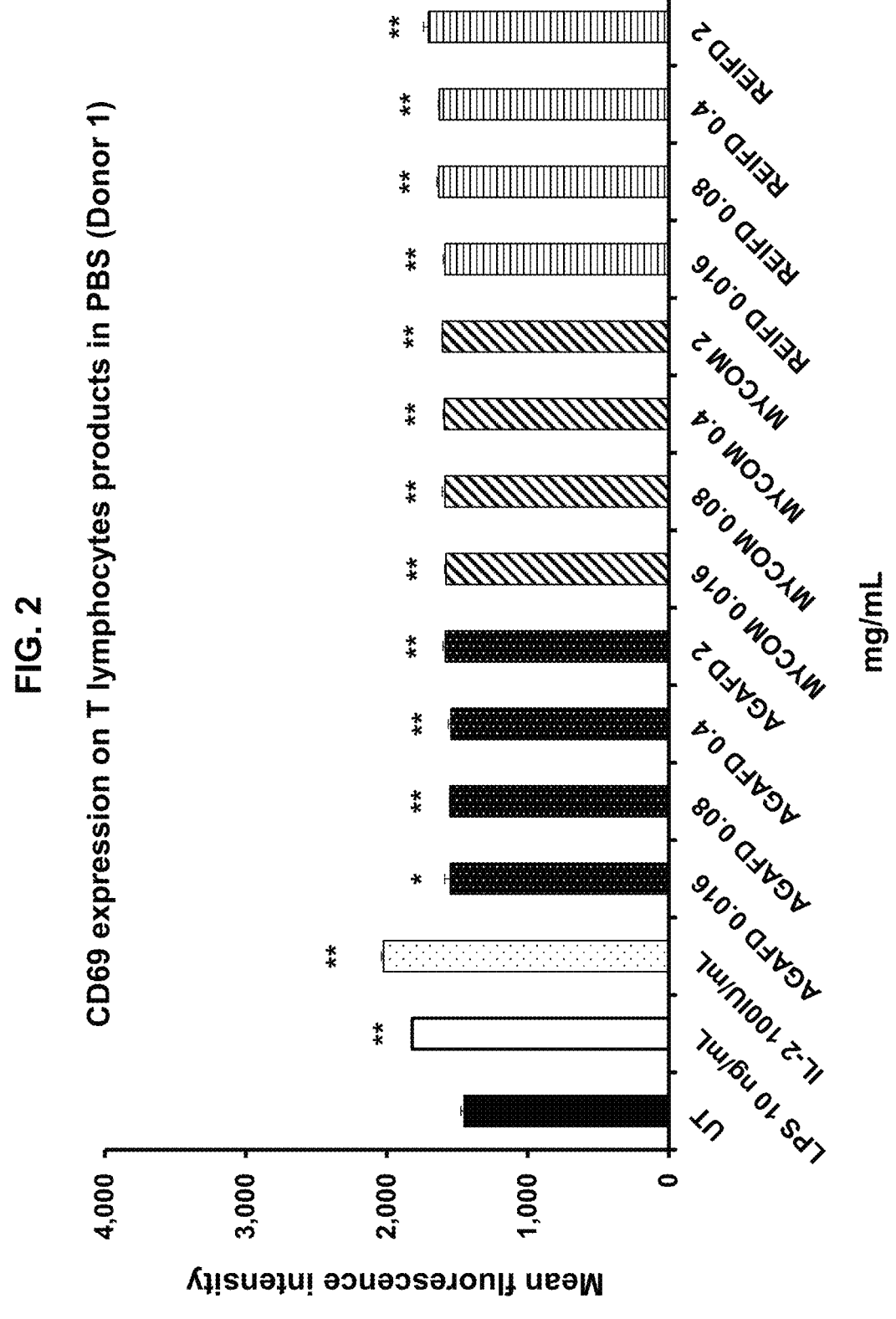
FIG. 2 shows CD69 expression on T cells in 24-hour whole blood cultures treated with products prepared in PBS (Donor 1). The LPS and IL-2 controls (tested at a single dose) are plotted for comparison. Statistical significance is indicated on the bar graph (* $p < 0.05$, ** $p < 0.01$). Abbreviations: Agarikon freeze dried (AGAFD), MyCommunity (MYCOM), Reishi freeze dried (REIFD).

Described herein are compositions and methods for treating and/or alleviating symptoms of adverse reactions, such as an increased anti-inflammatory response, triggered by infectious diseases or conditions. Current therapies for the treatment of increased anti-inflammatory responses, such as cytokine storm, aim to dampen the immune system response. The treatments include blocking specific cytokines, such as IL-6 with tocilizumab or siltuximab, and generalized immunosuppressive drugs, such as corticosteroids. However, immunosuppressive drugs are accompanied by many negative side effects such as increasing susceptibility to infections and can interfere with anti-cancer immunotherapies. Recently, COVID-19 has been shown to cause cytokine storm and potentially causing death. Thus, there remains a need for alternative medicines that have decreased side effects and can be used in all patients. Polysaccharides in mushrooms have been shown to initiate an immune response, sparking activity of TNF-α, IL-1β, IL-6, and other pro-inflammatory proteins involved in acute immune activation. Concern has been raised regarding isolated polysaccharide extracts and induction of IL-1β, an inflammatory cytokine that may exacerbate the runaway inflammatory presentations in later stages of COVID-19. However, we have shown that other biologically active compounds in mushrooms and mycelium (such as the sterols, phenols, and other terpenoid compounds) are important for the resolution of this inflammatory response, inducing anti-inflammatory cytokines such as IL-10 and IL-1ra. Therefore, it is surprising that an unextracted whole mushroom mycelium complex impacts the immune system in a balanced and modulatory manner and may decrease cytokine storm. *Fomitopsis offi-*

*cinalis* may modulate the harmful inflammation as described herein. *Fomitopsis officinalis* (also known as agarikon and *Laricifomes officinalis*) is a perennial polypore that grows on various coniferous trees in the Northern hemisphere. Typically found in old-growth forests, this brown-rot fungus decays woody tissue with its mycelium and produces massive conks that grow over many decades. *F. officinalis* has a long history of use in European and Indigenous American cultural and medicine traditions.

As used herein, the terms "comprise(s)," "include(s)," "having," "has," "can," "contain(s)," and variants thereof, to be open-ended transitional phrases, terms, or words that do not preclude the possibility of additional acts or structures. As used herein, the terms "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified. The term "or" can be conjunctive or disjunctive. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "about" as used herein refers to any values, including both integers and fractional components that are within a variation of up to ±10% of the value modified by the term "about." In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, in some embodiments within 5-fold, and in some embodiments within 2-fold, of a value.

As used herein, all percentages (%) used for compositions or formulations refer to mass (or weight, w/w) percent unless noted otherwise.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

As used herein, the terms "control," "reference level," and "reference" are used interchangeably and refer to a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of a patient group. ROC analysis, as generally known in the biological arts, is a determination of the ability of a test to discriminate one condition from another, e.g., to determine the performance of each marker in identifying a patient having COVID-19. A description of ROC analysis is provided in P. J. Heagerty et al., *Biometrics* 56: 337-44 (2000), the disclosure of which is hereby incorporated by reference in its entirety. Alternatively, cutoff values may be determined by a quartile analysis of biological samples of a patient group. For example, a cutoff value may be determined by selecting a value that corresponds to any value in the $25^{th}$-$75^{th}$ percentile range, in some embodiments a value that corresponds to the $25^{th}$ percentile, the 50th percentile or the $75^{th}$ percentile, and in some embodiments the $75^{th}$ percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC). The healthy or normal levels or ranges for a target or for a protein activity may be defined in accordance with standard practice. A control may be a subject or cell without an agonist as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

The term "dose" as used herein denotes any form of the active ingredient formulation or composition that contains an amount sufficient to produce a therapeutic effect with at least a single administration. "Formulation" and "composition" are used interchangeably herein.

The term "dosage" as used herein refers to the administering of a specific amount, number, and frequency of doses over a specified period of time, typically 1 day.

As used herein, the terms "effective amount," "therapeutically effective amount," or "therapeutically effective rate(s)" refers to a substantially non-toxic, but sufficient amount or delivery rates of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. It is understood that various biological factors may affect the ability of an agent to perform its intended task. Therefore, an "effective amount," "therapeutically effective amount," or "therapeutically effective rate(s)" may be dependent in some instances on such biological factors. For example, the precise determination of what would be considered an effective dose may be based on factors individual to each patient, including, but not limited to, the patient's age, size, type or extent of disease, stage of the disease, route of administration, the type or extent of supplemental therapy used, ongoing disease process and type of treatment desired (e.g., aggressive vs. conventional treatment). Further, while the achievement of therapeutic effects may be measured by a physician or a qualified medical practitioner using evaluations known in the art, it is recognized that individual variation and response to treatments may make the achievement of therapeutic effects a subjective decision. An appropriate "effective" amount in any individual case may be determined using techniques, such as a dose escalation study. The dose could be administered in one or more administrations. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, a mixture including at least two ingredients (e.g., water and Fo) and is itself a composition or formulation.

As used herein, the terms "inhibit," "inhibition," or "inhibiting" refer to the reduction or suppression of a given condition, symptom, or disorder, or disease, or a significant decrease in the baseline activity of a biological activity or process.

As used herein, a subject is "in need of" a treatment if such subject would benefit biologically, medically, or in quality of life from such treatment.

As used herein, the term "preventing" refers to a reduction in the frequency of, or delay in the onset of, symptoms of the condition or disease.

As used herein, the term "prophylaxis" refers to preventing or reducing the progression of a disorder, either to a statistically significant degree or to a degree detectable to one skilled in the art.

As used herein, the terms "sample" or "test sample" refers any sample in which the presence and/or level of a target is to be detected or determined or any sample treated with the compositions as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the terms "subject," "study participant," "participant," and "patient" interchangeably refer to any vertebrate, including, but not limited to, a mammal that wants or is in need of the herein described compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male. The subject may be female. In some embodiments, the subject has a specific genetic marker. The subject may be undergoing other forms of treatment.

As used herein, the term "substantially" means to a great or significant extent, but not completely.

As used herein, the terms "therapeutic composition" and "pharmaceutical composition" can be used interchangeably and refer to a combination of at least two ingredients.

As used herein, the terms "treat," "treating," or "treatment" of any disease or disorder refer to ameliorating the disease or disorder (i.e., slowing or arresting or reducing the development of the disease or at least one of the clinical symptoms thereof). In an embodiment, "treat," "treating," or "treatment" refers to alleviating or ameliorating at least one physical parameter including those which may not be discernible by a subject.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, mycology, microbiology, genetics, and protein and nucleic acid chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Various embodiments of the disclosure are described herein. It will be recognized that features specified in each embodiment may be combined with other specified features, including as indicated in the embodiments below, to provide further embodiments of the present disclosure.

It is understood that in the following embodiments, combinations of substituents or variables of the depicted formulae are permissible only if such combinations result in stable compounds.

Cytokine Storm

The term "increased anti-inflammatory response" as used herein refers to an exacerbated immune response to an infection, therapeutic, or autologous or allogeneic cells and tissues. The increased anti-inflammatory response may be a dysregulated pro-inflammatory cytokine response to an infection, therapeutic, or autologous or allogeneic cells and tissues. The increased anti-inflammatory response includes the rapid release of pro-inflammatory and anti-inflammatory cytokines, where the release of these initial cytokines can lead to an inflammatory cascade. The increased anti-inflammatory response may be a cytokine storm.

As used herein, the terms "cytokine storm," "cytokine release syndrome," "macrophage activation syndrome," and "hemophagocytic lymphohistiocytosis" interchangeably refer to the dysregulation of pro-inflammatory and anti-inflammatory cytokines leading to disease. A cytokine storm may be referred to as being part of a sequence because one cytokine typically leads to the production of multiple other cytokines that can reinforce and amplify the immune response. Cytokine storm is a potentially life-threatening cytokine-associated toxicity. Diagnosing and management of cytokine storm is routinely based on clinical parameters and symptoms, such as identifying biomarkers (e.g., gene products (e.g., polypeptides, gene expression and/or protein expression profiles), or other analytes). Cytokine storm results from high-level immune activation when large numbers of lymphocytes and/or myeloid cells release inflammatory cytokines upon activation. The severity of the cytokine storm and the timing of onset of symptoms can vary depending on the magnitude of immune cell activation. The pro-inflammatory mediators involved in cytokine storm are divided into two subgroups: early mediators and late mediators. The transcription factor interferon regulatory factor 5 (IRF5) is critical for pro-inflammatory cytokine production. The inflammatory response to influenza infection is known to increase glucose metabolism. Glucose metabolism is required for activating IRF5-induced cytokine production, specifically the hexosamine biosynthesis pathway. Hexosamine biosynthesis results in the end product uridine diphosphate N-acetylglucosamine (UDP-GlcNAc). Through O-GlcNAcylation, UDP-GlcNAc is added to proteins to modify their activity. It has been shown that O-GlcNAcylation of IRF5 is necessary for IRF5-mediated cytokine production. It also has been shown that influenza patients have higher blood glucose levels and more O-GlcNacylation of IRF5 than healthy controls and that blood glucose levels are highly correlated with levels of inflammatory cytokines. Therefore, glucose metabolism plays a role in the development of cytokine storm.

Disease conditions commonly associated with a cytokine storm include but are not limited to: sepsis, systemic inflammatory response syndrome (SIRS), cachexia, septic shock syndrome, traumatic brain injury (e.g., cerebral cytokine storm), graft versus host disease (GVHD), or the result of treatment with activated immune cells, e.g., IL-2 activated T cells, T cells activated with anti-CD19 Chimeric Antigen Receptor (CAR) T cells. Infectious diseases commonly associated with cytokine storm include viral, bacterial, and parasitic infections. The viral infectious diseases include, but are not limited to, Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), Herpesviridae (human herpes viruses, Varicella zoster virus, Epstein-Barr virus, cytomegalovirus), avian influenza, smallpox, pandemic influenza, adult respiratory distress syndrome (ARDS). CoV can include one or more of Severe Acute Respiratory Syndrome (SARS-CoV), Middle East Respiratory Syndrome (MERS-CoV), COVID-19 (2019-nCoV, SARS-CoV-2), 229E, NL63, 0043, or HKU1. The bacterial infectious diseases include, but are not limited to, *Streptococcus pneumoniae, Mycobacterium tuberculosis, Bordetella pertussis, Haemophilus influenzae, Moraxella catarrhalis, Pseudomonas aeruginosa, Stenotrophomonas maltophila, Staphylococcus aureus, Streptococcus pyogenes, Neisseria meningitidis, Klebsiella pneumoniae,* or Non-tuberculosis *Mycobacterium*. The parasitic infectious diseases include, but are not limited to, malaria.

Coronaviruses (CoVs), are enveloped positive-sense RNA viruses, which are surrounded by crown-shaped, club-like spike projections on the outer surface. Coronaviruses' spike proteins are glycoproteins that are embedded over the viral envelope. This spike protein attaches to specific cellular receptors and initiates structural changes of spike protein, and causes penetration of cell membranes, which results in the release of the viral nucleocapsid into the cell. These spike proteins determine host trophism. Coronaviruses have a large RNA genome, ranging in size from 26 to 32 kilobases and capable of obtaining distinct ways of replication. Like other RNA viruses, coronaviruses under-go replication of the genome and transcription of mRNAs upon infection. Coronavirus infection in a subject can result in significant and long-term damage of the lungs, leading to possibly sever respiratory issues.

As used herein "2019-nCoV" is a betacoronavirus (Beta-CoV or β-CoV). In particular, 2019-nCoV is a Beta-CoV of lineage B. 2019-nCoV may also be known as SARS-CoV-2 or 2019 novel coronavirus. Betacoronaviruses are one of four genera of coronaviruses and are enveloped, positive-sense, single-stranded RNA viruses of zoonotic origin. Betacoronaviruses mainly infect bats, but they also infect other species like humans, camels, and rabbits. 2019-nCoV may be transferable between animals, such as between humans. As used herein "viral transmission" is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The overall structure of β-CoV genome contains an ORF1ab replicase polyprotein (rep, pp1ab) preceding other elements. This polyprotein is cleaved into many nonstructural proteins. 2019-nCoV has a phenylalanine in the (F486) in the flexible loop of the receptor binding domain, flexible glycyl residues, and a four amino acid insertion at the boundary between the S1 and S2 subunits that results in the introduction of a furin cleavage site. The furin cleavage site may result in 2019-nCoV tissue tropism, increase transmissibility, and alter pathogenicity.

Diagnosis of 2019-nCoV may comprise a positive test for 2019-nCoV and/or onset of 2019-nCoV symptoms, or combinations thereof. Symptoms of 2019-nCoV include, but are not limited to, one or more of the following symptoms: nasal congestion, sore throat, fever, body aches, exhaustion, dry cough, difficulty breathing, loss of taste, loss of smell, or a combination thereof. The methods and compositions herein can recover or aid in the recovery of taste and smell. Subjects may also experience long-term effects from COVID-19, where symptoms can persist for weeks or months after the initial infection and disappear and reappear after infection. Long-term COVID-19 symptoms include, but are not limited to, one or more of shortness of breath, cough, fatigue, joint pain, chest pain, difficulty with thinking and/or concentration (i.e. "brain fog"), depression, anxiety, changes in mood, muscle pain, headache, intermittent fever, heart palpitations, inflammation of the heart, lung function abnormalities, acute kidney injury, rash, hair loss, smell and/or taste problems, sleep issues, and difficulty with memory. Subjects who experience long-term effects from COVID-19 are known as long-haulers. The methods and compositions herein may treat long-term COVID-19 or decrease the symptoms thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

Symptoms of cytokine storm can include neurologic toxicity, disseminated intravascular coagulation, cardiac dysfunction, adult respiratory distress syndrome, renal failure, and/or hepatic failure. For example, symptoms of cytokine storm can include fever with or without rigors, fatigue, malaise, myalgias, vomiting, headache, nausea, anorexia, arthralgias, diarrhea, rash, hypoxemia, tachypnea, hypotension, widened pulse pressure, potentially diminished cardiac output (late), increased cardiac output (early), azotemia, hypofibrinogenemia with or without bleeding, elevated D-dimer, hyperbilirubinemia, transaminitis, confusion, delirium, mental status changes, hallucinations, tremor, seizures, altered gait, word finding difficulty, frank aphasia, elevated heart rate, coagulopathy, MODS (multiple organ dysfunction syndrome), cardiovascular dysfunction, distributive shock, cardiomyopathy, hepatic dysfunction, renal dysfunction, encephalopathy, clinical seizures, respiratory failure, tachycardia, or dysmetria.

IL-6 is thought to be a mediator of cytokine storm toxicity. High IL-6 levels may initiate a proinflammatory IL-6 signaling cascade, leading to one or more of the cytokine storm symptoms. IL-6 and sIL-6R levels can be measured for example, by methods described in Chen et al. Chen et al., *J. Immunol. Meth.* 434:1-8 (2016). In some cases, the level of C-reactive protein (CRP) (a biomolecule produced by the liver, e.g., in response to IL-6) can be a measure of IL-6 activity. In some cases, CRP levels may increase several-fold (e.g., several logs or orders of magnitude) during cytokine storm. CRP levels can be measured using standard methods available in the art. Spiking IL-6 is dangerous for COVID-19 as it potentiates a cytokine storm, therefore current clinical trials aim to suppress IL-6 in COVID-19 patients. The compositions described herein spike IL-6 while simultaneously spiking IL-10 and IL-1ra, and therefore surprisingly reduce cytokine storms, neuroinflammation, and blood clotting.

Rapidly proliferating and highly activated T-cells or natural killer (NK) cells that result in the exaggerated release of cytokines during a cytokine storm can include more than 150 inflammatory mediators such as cytokines, oxygen free radicals, and coagulation factors. Both pro-inflammatory cytokines (such as TNF-α, IL-1, and IL-6) and anti-inflammatory cytokines (such as IL-10, and IL-1 receptor antagonist (IL-1RA)) become greatly elevated in, for example, serum. It is this excessive release of inflammatory mediators that triggers the cytokine storm.

A "pro-inflammatory cytokine" or a "pro-inflammatory mediator" is an immuno-regulatory cytokine that induces inflammation. A pro-inflammatory cytokine may upregulate or increase the synthesis of secondary pro-inflammatory mediators and other pro-inflammatory cytokines by immune cells. In addition, pro-inflammatory cytokines can stimulate production of acute phase proteins that mediate inflammation and attract inflammatory cells. Pro-inflammatory cytokines that are generally responsible for early immune responses include IL-1, IL-6, and TNF-α. IL-1, IL-6, and TNF-α are also considered endogenous pyrogens as they contribute to increasing body temperature. Other examples of pro-inflammatory cytokines or pro-inflammatory mediators include IL-2, IL-4, IL-5, IL-6, IL-7, IL-8, IL-9, IL-11, IL-12p70, IL-13, IL-15, IL-17A, IL-18, interferon (IFN)-γ, monocyte chemoattractant protein (MCP) 1, eotaxin, interferon gamma-induced protein (IP) 10, granulocyte colony-stimulating factor (GM-CSF), macrophage inflammatory protein (MIP) 1α, MIP 1β, RANTES, leukemia, inhibitory factors (LIF), oncostatin M (OSM), and a variety of chemokines that attract inflammatory cells.

IL-1 is an important pro-inflammatory cytokine. IL-1 is a soluble protein having a mass of approximately 17 kilo-Daltons (kD). IL-1 is produced by a variety of cells, for example macrophages, white blood cells, lymphocytes, monocytes, dendritic cells, and accessory cells that are involved in activation of T-lymphocytes and B-lymphocytes. IL-1 is typically released by such cells during an immune response. IL-1 is generally considered to be a pro-inflammatory cytokine. The original members of the IL-1 superfamily are IL-1α, IL-β, and IL-1 receptor antagonist (IL-1RA). Both IL-1a and IL-1β play important roles in the inflammatory response of the body against pathogens or infection and recognize the same IL-1 receptor and perform similar biological functions. IL-1a is predominantly a cell-associated molecule whereas IL-1β is generally a secreted molecule. The term "IL-1" as used herein includes one or both of IL-1α and IL-1β. IL-1 can increase the expression of adhesion factors on endothelial cells to enable transmigration of leukocytes to sites of infection. In addition, IL-1 can stimulate the hypothalamus thermoregulatory center to cause an increase in body temperature (i.e., a fever). In particular, IL-1β is involved in a range of cellular activities such as cell proliferation, cell differentiation, cell apoptosis, and pain. TNF-α is involved in systemic inflammation and works in tandem with a variety of other cytokines to stimulate the acute phase immune reaction. TNF-α can induce apoptotic cell death as well as inhibit tumorigenesis and viral replication. TNF-α and IL-1 can work simultaneously and synergistically in stimulating and sustaining inflammation within the body.

"Anti-inflammatory cytokines" or "anti-inflammatory mediators" refer generally to immuno-regulatory cytokines that inhibit or counteract various aspects of inflammation. In other words, anti-inflammatory cytokines counteract various biological effects of pro-inflammatory cytokines and pro-inflammatory mediators. Anti-inflammatory cytokines can control or mitigate the magnitude of inflammation. Functions of anti-inflammatory cytokines include inhibiting production of pro-inflammatory cytokines and inhibiting cell activation. Examples of anti-inflammatory cytokines include, but are not limited to, IL-1RA, IL-2, IL-4, IL-7, IL-9, IL-10, IL-13, or IL-15. IL-2 is a variably glycosylated single protein molecule having as mass of approximately 15.5 kD. IL-2 is generally produced by activated T helper cells (also known as effector T cells) during an immune response. Pathogens (also known as antigens) that invade or are introduced within the body bind to receptors that are found on the surfaces of lymphocytes. Binding of such pathogens or antigens to T cell receptors (TCR) stimulates secretion of IL-2. IL-2 mediates its effects by binding to IL-2 receptor molecules, which are expressed by lymphocytes. The binding of IL-2 to its receptor molecule triggers a signaling cascade, for example Ras/MAPK, JAK/Stat, and PI 3-kinase/Akt signaling modules. IL-2 has numerous functions including facilitating production of immunoglobulins (Ig) by B cells. In addition, IL-2 induces differentiation and proliferation of NK cells and stimulates growth, differentiation, and proliferation of antigen-selected cytotoxic T cells via induction gene expression. IL-2 is considered to be important for the development of T cell immunologic memory and is necessary during T cell development in the thymus for enabling the maturation of regulatory T cells.

Given the mutability of viruses as they jump from host to host, many variants of viruses can evolve and emerge, with some becoming more damaging and deadlier. Although vaccines and antiviral drugs can be effective against one strain of virus when they are designed and tested, these continuous mutations can result in vaccine evasion or loss in drug potency. Viruses or other pathogens that can evade the efficacy of vaccines and drugs, make these disease agents more virulent, more contagious, and ultimately more deadly to those infected. Hence, by augmenting immunity while downregulating specific cytokines can help not only lessen the degree of infection but also prevent cytokine storms, making vaccines, anti-viral drugs and other treatments more effective. The methods and compositions described herein, in conjunction with conventional therapies such as vaccines and antiviral drugs, may potentiate the recovery of patients infected with viruses such as COVID, flu viruses and other known viruses, due to the immune enhancement properties coupled with the anti-inflammatory effects of the methods and compositions described herein, and the stimulation of IL-10 and IL1ra by the methods and compositions described herein. Moreover, the use of the methods and compositions as described herein can help enhance innate immunity of patients who suffer from viruses that are immune evasive. Examples of immune evasion include but are not limited to cancer-causing viruses (oncoviruses) that are responsible for Merkel Cell Carcinoma, and the many forms of human papillomavirus (HPV) and Herpes induced cancers. In essence, these mushroom adjuvant therapies described herein can enhance innate immune system, helping decloak or sensitize these disease agents and in some cases the cancers they cause, while augmenting better immune detection, targeting, and vaccine/drug efficacy—enhancing recovery. The methods and compositions herein can enhance a wide range of conventional therapies currently in practice for fighting viral and microbial diseases. Conventional viral therapies include, but are not limited to, vaccines such as live attenuated virus vaccines, attenuated virus vaccines, mRNA vaccines, cell-based vaccines, recombinant vaccines, adjuvant vaccines, or quadrivalent vaccines; and antiviral drugs such as oseltamivir (Tamiflu), zanamivir (Relenza), peramivir (Rapivab) or baloxavir (Xofluza).

Pain and Cytokines

A unique combination of molecular and cellular factors can lead to acute and chronic pain conditions with varying pathologies. Pain can be categorized into the following broad categories: inflammatory, neuropathic, and syndrome-based (e.g., fibromyalgia). There is overlap between these generalized categories. For example, inflammation can result in nerve damage, nerve injury involves inflammation, and syndrome-based pain can be neuropathic or inflammatory or both. Inflammatory pain occurs with peripheral tissue damage and the resulting tissue inflammation. Alternatively, neuropathic pain results from direct damage to nerves in the peripheral or central nervous systems. Postoperative pain has both inflammatory and neuropathic qualities. It is widely recognized that postoperative pain occurs as a result of the direct cutting of tissues and peripheral nerves at the surgical site. Examples of pain conditions include pain associated with psychological conditions, pain associated with infections (e.g., bacterial or viral infections), abdominal pain, abnormal gastrointestinal motility pain, acute herpes zoster pain, acute inflammatory pain, acute intermittent pain, acute musculoskeletal pain, acute obstetric pain, acute pain, acute post-operative pain (e.g., bunionectomy pain; abdomino-plasty pain; knee pain from a total knee replacement; hip pain from a total hip replacement; pain from a laminectomy; pain from a hernia repair; or hemorrhoid removal pain), acute tendonitis pain, acute visceral pain, adiposis dolorosa pain, amyotrophic lateral sclerosis pain, angina-induced pain, anti-retroviral therapy induced neuralgia, anxiety pain, appendicitis pain, arrhythmia pain, arthritis pain, ataxia pain, back pain, Behçet's disease pain, bipolar disorder pain, bladder and urogenital disease pain, bone pain, bowel obstruction pain, brachial plexus avulsion injury pain, break-through pain, burn pain, burning mouth syndrome pain, bursitis pain, cancer chemotherapy induced neuralgia, can-cer pain, cardiac arrhythmia pain, cardiac pain, carpal tunnel syndrome pain, central pain, cerebral ischemia, Cesarean-section pain, Charcot-Marie Tooth neuropathic pain, che-motherapy induced neuropathic pain, chest pain, cholecys-titis pain, chronic and acute headache pain, chronic and acute neuropathic pain, chronic arthritis, chronic pain, chronic visceral pain, cluster headache pain, cold pain, complex regional pain syndrome, Crohn's disease pain, dental pain (e.g., third molar extraction), depression pain, diabetic neuralgia, diabetic neuropathic pain, diabetic peripheral neuropathic pain, drug therapy induced neuralgia, ectopic proximal and distal discharge pain, endometriosis pain, epilepsy pain, erythromelalgia pain, exercise induced angina pain, exercise induced pain, exercise pain, Fabry's disease pain, femur cancer pain, fibromyalgia pain, general neuralgias, granuloma annulare pain, Guillain-Barre pain, gut pain, Haglund syndrome pain, head pain, headache pain, hereditary sensory neuropathic pain, hernia pain, herpetic neuralgia pain, HIV-associated neuropathic pain, HIV-asso-ciated sensory neuropathic pain, hyperactivity bladder pain, hypertension pain, idiopathic pain, idiopathic sensory neu-ropathic pain, idiopathic small-fiber neuropathic pain, incontinence pain, inflammatory bowel disease pain, inflam-matory pain, injury pain, interstitial cystitis (IC) pain, intes-tinal obstruction pain, intractable pain, irritable bowel syn-drome pain, joint pain, labor pain, leprosy pain, lipoidica pain, malignancy pain, mechanical low back pain, migraine pain, Morton's neuroma pain, movement disorder pain, multiple sclerosis (MS) pain, musculoskeletal pain, myofas-cial pain syndrome pain, myotonia pain, neck pain, necro-biosis pain, nerve avulsion injury pain, nerve entrapment injury pain, neurodegenerative disorder pain, neuroendo-crine disorder pain, neuropathic low back pain, neuropathic pain, nociceptive pain, non-malignant chronic bone pain, orofacial pain, osteoarthritis pain, painful bladder syndrome, painful legs, painful moving toes, painful neuromas, palpi-tations, pancreatic pain, paroxysmal extreme pain, patho-logical cough pain, pelvic pain, peripheral nerve injury pain, phantom pain, phlebitic pain, post spinal cord injury pain, post-amputation pain, post-herpetic neuralgia, post-mastec-tomy pain, post-stroke pain, postsurgical pain, premenstrual pain, prostatitis pain, pruritis pain, psychiatric disorder associated pain, pyelonephritis pain, radicular pain, radicu-lopathy, radiotherapy-induced neuropathic pain, renal colic pain, rheumatoid arthritis pain, sarcoidosis pain, sciatica pain, severe pain, shingles pain, sickle cell anemia pain, sinusitis pain, soft tissue pain, spinal cord injury pain, spinal stenosis pain, sports injury pain, stress-induced angina pain, stress-induced pain, stroke pain, temporomandibular joint pain, tendonitis pain, tension headache pain, thalamic pain, tinnitus pain, trauma pain, traumatic brain injury pain, traumatic neuroma, trigeminal autonomic cephalalgia, trigeminal neuralgia, tumor pain, urinary incontinence pain, visceral pain, widespread pain, or other types of pain.

There is a robust immune response in pain conditions and following injury that includes infiltration of neutrophils, macrophages, and lymphocytes. The immune response aids in wound healing, but also results in sensitization of sensory neurons to various stimuli such as mechanical and heat stimuli. When an injury occurs in the periphery, the immune response begins at the site of tissue damage and moves proximally to the dorsal root ganglia and spinal cord. Immune cells interact with sensory neurons and activate canonical immune receptors expressed by neurons in both the peripheral and central nervous systems. For example, neurons express immune receptors such as toll-like receptors (e.g., TLR4, TLR9) and cytokine receptors for cytokines such as TNF-α, IL-1, IL-6, IL-10, IL-1RA, etc. Components of the innate immune system have emerged as crucial mediators in the development and maintenance of hyper-sensitivity following nerve injury.

Compounds

In one embodiment described herein, the composition comprises an aqueous or solid fraction of a mycelium or fruit body, a fermented substrate thereof, or a combination thereof. In one aspect, the extract comprises a mixture of compounds or isolated compounds comprising one or more of acetovanillone, baeocystin, (4-phosphoryloxy-N-methyl-tryptamine), beta-sitosterol, caffeic acid, cannabidiol, can-nabichromene, cannabigerol, Δ8-tetrahydrocannabinol, Δ9-tetrahydrocannabinol, cannabinol, tetrahydrocannabi-varin, cannabidiol-2',6'-dimethyl ether, chrysin, cordycepin, cordysinin, davallialactone, dehydrosulphurenic acid, ebu-ricoic acid, ellagic acid, ergosterols, Erinacine A, Erinacine B, Erinacine C, Erinacine D, Erinacine E, Erinacine F, Erinacine G, Erinacine H, Erinacine I, Erinacine J, Erinacine K, Erinacine P, Erinacine Q, Erinacine R, erinacines, erina-col, ethyl 7-chloro-2-oxo-4-phenyl-2H-chromen-3-carboxy-late, ethyl vanillin, eugenol, ferulic acid, gallic acid, guai-acol, glucans, β-glucans, harmane, harmine, harmol, Hericenone A, Hericenone B, Hericenone C, Hericenone D, Hericenone E, Hericenone F, Hericenone G, Hericenone H, hericenones, hexanal, hispidin, hispolons, 4-hydroxyben-zoic acid, 4-hydroxytryptamine, hypholomine B, inoscavin A, inotodiol, lanosterol, linoleic acids, N,N-dimethyltrypt-amine, norbaeocystin (4-phosphoryloxy-tryptamine), norharmine, norpsilocin (4-hydroxy-N-methyl-tryptamine), p-coumaric acid, perlolyrine, phelligridin D, p-hydroxyben-zaldehyde, p-hydroxybenzoic acid, protocatechuic acid, psi-locin (4-hydroxy-N,N-dimethyltryptamine), psilocybin (4-phosphoryloxy-N,N-dimethyltryptamine), quercetin, rutin, shikimic acid, sinapinic acid, stigmasterol, sul-phurenic acid, syringic acid, trametenolic acid, trans-cin-namic acid, trans-coumaric acid, trans-ferulic acid, tryptam-ines, vanillic acid, β-carbolines, alkaloids, amino acids, anthranilic acid alkaloids, apiole, (+)-aromanderndrene, asa-rone, aurones, benzofuranoids, benzofurans, benzophe-nones, benzopyranoids, benzopyrans, benztropolones, cis-α-bergamotene, trans-α-bergamotene, α-bisabolol, borneol, γ-cadinene, caffeic acid, camphor, carbohydrates, carote-noids, 3-carene, β-carbolines, trans-β-caryophyllene, cat-echins, chalcones, chavicol, chavicols, chromones, cineol, cinnamic acid, cinnamic aldehydes, cinnamic monolignols, conferyl alcohol, coniferyl alcohol, cordysinin, coumarins, coumaric acid, coumaryl alcohol, cutin, depsides, depsi-dones, dillapiole, diterpenes, diterpenoids, γ-elemene, elemicin, eleutherosides, esterterpenoids, estragole, eudes-man-3,7(11)-diene, β-eudesmol, γ-eudesmol, eugenol, trans-β-farnesene, ferulic acid, haramane, harmine, norharmine, harmol, α-humuline, β-fenchol, 5-hydroxyferulic acid, fla-vonoids, glycopeptides, hydroxycinnamic acids, hydroxylated fatty acids, imidazole alkaloids, isoflavonoids, isoquinoline alkaloids, β-lactams, lignans, limonoids, R-limonene, (−)-linalool, lipids, lysine alkaloids, meroterpenoids, methyl eugenol, miscellaneous terpenoids, monoterpenoid indole alkaloids, monoterpenoids, myrcene, myristicin, nerolidol, nicotinic acid alkaloids, cis-ocimene, 1-octanol, ornithine alkaloids, otenoids, oxazole alkaloids, oxygen heterocycles, peptides, phellanderene, phenolics, phenylalanine alkaloids, phenylpropanoids, phenylpropanoids, phenylpropenes, perlolyrine, pinene, polycyclic aromatic natural products, polyketide alkaloids, polyketides, polypyrroles, ptteridines, purines, putrescine alkaloids, pyrazine alkaloids, pyrimidines, pyrrole alkaloids, quassinoids, quinonemethides, quinones, quinoxaline alkaloids, resveratrol, trans-resveratrol, cis-sabinene hydrate, safrole, γ-selinene, semiochemicals, septide alkaloids, sesquiterpenes, sesquiterpenoids, simple aromatic natural products, sinapic acid, sinapyl alcohols, spermidine alkaloids, spermine alkaloids, sporopollenin, steroidal alkaloids, steroids, sterols, stilbenes, stilbenoids, suberin, tannins, terpenoid alkaloids, terpenoids, γ-terpinene, α-terpineol, terpinolene, tetraterpenoids, thiazole alkaloids, triterpenes, triterpenoids, tryptophan alkaloids, tyrosine alkaloids, umbelliferone, xanthone, or pharmaceutically acceptable salts, hydrates, solvates, prodrugs, stereoisomers, or tautomers thereof, or combinations thereof.

Pharmaceutically Acceptable Salts

Pharmaceutically acceptable salts of the compounds described herein are also contemplated for the uses described herein. As used herein, the terms "salt" or "salts" refer to an acid addition or base addition salt of a compound described herein. "Salts" include in particular "pharmaceutical acceptable salts." The term "pharmaceutically acceptable salts" refers to salts that retain the biological effectiveness and properties of the compounds disclosed herein and, which typically are not biologically or otherwise undesirable. In many cases, the compounds disclosed herein can form acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, and tromethamine.

Another embodiment is one or more compounds of *Fomitopsis officinalis* or *Trametes versicolor* as an acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, glucceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate, or xinafoate salt form.

Pharmaceutical Compositions

Another embodiment is a pharmaceutical composition comprising *Fomitopsis officinalis, Trametes versicolor*, or *Hericium erinaceus*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers. The term "pharmaceutically acceptable carrier" refers to a pharmaceutically acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient.

Pharmaceutical excipients useful for the compositions as described herein comprise: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, phosphate buffer saline); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein. See Remington's Essentials of Pharmaceutics, Pharmaceutical Press Publishing Company, London, UK, 1st Edition, 2013, and the Handbook of Pharmaceutical Excipients, $8^{th}$ Edition, Pharmaceutical Press Publishing Company London, U K, 2017, each of which is incorporated by reference herein for such teachings.

Certain compounds described herein may exist in particular geometric or stereoisomeric forms. A particular enantiomer of a compound described herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Another embodiment is a method for manufacturing a dosage form comprising formulating a composition as described herein comprising sprays, capsules, tablets, elixirs, emulsions, lozenges, suspensions, syrups, pills, lotions, epidermal patches, suppositories, inhalers, or injectables. Any methods known to the art for formulating extracts or active principal ingredients into lotions, soaps, etc. may be utilized. In some embodiments, the composition may be in the form of a capsule.

The compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally, or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween®, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions described herein may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be administered using a rectal suppository formulation (see above) or a suitable enema formulation. Topically transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutically acceptable compositions of this disclosure may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons, or other conventional solubilizing or dispersing agents. The amount of the compounds of the present disclosure that may be combined with the carrier materials to produce a composition in a single dosage form will vary depending upon the host treated and the mode of administration. Preferably, the compositions should be formulated so that a dosage of between 0.01-100 mg/kg body weight/day of the active ingredient can be administered to a patient receiving these compositions.

In some embodiments, the composition may include an aqueous or solid fraction of a mycelium or fruit body, a fermented substrate thereof, or a combination thereof. The mycelium or fruit body may be one or more of *Agaricus brasiliensis* f. *blazei*, *Cordyceps militaris*, *Flammulina velutipes*, *Fomes fomentarius*, *Fomitopsis officinalis*, *Ganoderma applanatum*, *Ganoderma lucidum* s.l., *Ganoderma oregonense* s.l., *Grifola frondosa*, *Hericium erinaceus*, *Inonotus obliquus*, *Lentinula edodes*, *Phellinus linteus*, *Piptoporus betulinus*, *Pleurotus ostreatus*, *Schizophyllum commune*, *Trametes versicolor*, *Psilocybe cubensis*, *Psilocybe azurescens*, or *Psilocybe cyanescens*. The mycelium or fruit body may be one or more of *Fomitopsis officinalis* or *Trametes versicolor*. The mycelium or fruit body may be *Fomitopsis officinalis*. The mycelium or fruit body may be *Trametes versicolor*. The mycelium or fruit body may be *Hericium erinaceus*. The aqueous or solid fraction of the mycelium, fermented substrate, or combination thereof may include beta-glucans. In one embodiment, the composition is described in Table 1.

TABLE 1

| Exemplary Compositions | | |
| --- | --- | --- |
| Component | Example | Dosage |
| Aqueous or solid fraction of a mushroom mycelium and/or fruit body mixture | *Agaricus blazei*, *Cordyceps militaris*, *Flammulina velutipes*, *Fomes fomentarius*, *Fomitopsis officinalis*, *Ganoderma applanatum* s.l., *Ganoderma lucidum* s.l., *Ganoderma oregonense* s.l., *Grifola frondosa*, *Hericium erinaceus*, *Inonotus* | 200 mg-10 g |

TABLE 1-continued

| Exemplary Compositions | | |
| --- | --- | --- |
| Component | Example | Dosage |
| | *obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens* | |
| Aqueous, ethyl acetate, or solid fraction of a mycelium, a fermented substrate thereof, or a combination thereof | *Agaricus blazei, Cordyceps militaris, Flammulina velutipes, Fomes fomentarius, Fomitopsis officinalis, Ganoderma applanatum* s.l., *Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens* | 200 mg-10 g |
| Aqueous, hydroethanolic, or ethanolic extract of a mycelium | *Agaricus blazei, Cordyceps militaris, Flammulina velutipes, Fomes fomentarius, Fomitopsis officinalis, Ganoderma applanatum* s.l., *Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens* | 200 mg-10 g |
| Dried mycelium powder | *Agaricus blazei, Cordyceps militaris, Flammulina velutipes, Fomes fomentarius, Fomitopsis officinalis, Ganoderma applanatum* s.l., *Ganoderma lucidum* s.l., *Ganoderma oregonense* s.l., *Grifola frondosa, Hericium erinaceus, Inonotus obliquus, Lentinula edodes, Phellinus linteus, Piptoporus betulinus, Pleurotus ostreatus, Schizophyllum commune, Trametes versicolor, Psilocybe cubensis, Psilocybe azurescens,* or *Psilocybe cyanescens* | 200 mg-10 g |
| Optional pharmaceutical excipients | Fillers, binders, solvents, diluents, vehicles, lubricants, preservatives, flavors, colors, buffering agents, etc. | 0.05-75% by weight |

Compositions can be liquid, suspensions, emulsions, dry powder admixtures, or combinations thereof In another embodiment, the composition may include an aqueous or solid fraction of a mycelium or fruit body, a fermented substrate thereof, or a combination thereof combined with an extract of one or more of *Agaricus augustus, Agaricus blazei, Agaricus bonardii, Agaricus brasiliensis, Agaricus campestris, Agaricus lilaceps, Agaricus subrufescens, Agaricus sylvicola, Agrocybe aegerita, Agrocybe arvalis, Agrocybe pediades, Agrocybe praecox, Antrodia cinnamonea, Clitocybe odora, Conocybe cyanopus, Conocybe lacteus, Conocybe rickenii, Conocybe smithii, Conocybe tenera, Coprinopsis lagopus, Coprinopsis nivea, Coprinus comatus, Coprinus micaceus, Fomitiporia robusta, Fomitopsis officinalis* (*Laricifomes officinalis*), *Ganoderma atrum, Ganoderma brownii, Ganoderma curtisii, Ganoderma lingzhi, Ganoderma oregonense, Ganoderma tsugae, Gymnopus hydrophilus, Gymnopus peronatus, Hericium erinaceus, Hericium coralloides, Hericium ramosum, Heterobasidion annosum, Hypholoma aurantiaca* (*Leratiomyces ceres*), *Hypholoma capnoides, Hypholoma sublateritium, Hypsizygus marmoreus, Hypsizygus tessulatus, Hypsizygus ulmarius, Inonotus andersonii, Inonotus dryadeus, Inonotus hispidus, Laetiporus cincinnatus, Laetiporus conifericola, Laetiporus sulphureus, Lentinus ponderosus, Lenzites betulina, Lepiota procera* (*Macrolepiota procera*), *Lepiota rachodes* (*Chlorophyllum rachodes*), *Lepista nuda, Mycena alcalina, Mycena auran-* *tiadisca, Mycena pura, Panaeolus foenisecii, Panaeolus subbalteatus, Panellus serotinus, Panellus serotinus, Panellus stipticus, Phellinus igniarius, Phellinus linteus, Phellinus pini, Piptoporus betulinus, Pleurotus columbinus, Pleurotus cystidiosus, Pleurotus ostreatus, Pleurotus pulmonarius, Pleurotus sapidus, Pleurotus tuberregium, Pluteus cervinus, Polyporus elegans, Psathyrella aquatica, Psathyrella condolleana, Psathyrella hydrophila, Psilocybe allenii, Psilocybe azurescens, Psilocybe caerulescens, Psilocybe coprophila, Psilocybe cubensis, Psilocybe cyanescens, Psilocybe ovoideocystidiata, Psilocybe stuntzii, Psilocybe subaeruginosa, Stereum complicatum, Stereum hirsutum, Stereum ostrea, Stropharia aeruginosa, Stropharia cyanea, Stropharia rugoso-annulata, Stropharia semiglobata, Stropharia semigloboides, Stropharia squamosa, Stropharia thrausta, Stropharia umbonotescens, Termitomyces robusta, Trametes aesculi, Trametes cingulata, Trametes ectypa, Trametes elegans, Trametes gibbosa, Trametes hirsuta, Trametes ochracea, Trametes pubescens, Trametes villosa, Volvaria bombycina, Volvariella volvacea, Wolfiporia cocos,* or combinations thereof.

In another embodiment, the composition may include an aqueous or solid fraction of a mycelium or fruit body, a fermented substrate thereof, or a combination thereof combined with one or more extracts or pure chemicals from plant species comprising one or more of *Bacopa* species (*Bacopa*

*monnien*), Gotu kola (*Centella asiatica*), and *Gingko* (*Gingko biloba*, Ginger (*Zingiber officinale*), Holy Basil (*Ocimum* sanctum), Hu Zhang (*Polygonum cuspidatum*), Oregano (*Origanum vulgare, Origanum onites*), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula spica* and related species in the genus *Lavandula*), skullcap (*Scutellaria lateriflora*) oat straw (*Avena sativa, Avena byzantina*), *Salvia divinorum*, aka Diviner's Sage, *Banisteriopsis caapi* and *Psychotria* species, plants containing ibogaine (*Tabemanthe iboga, Voacanga africana* and *Tabemaemontana undulate*), peyote (*Lophophora williamsii*), the seeds of morning glory (*Ipomoea tricolor* and related species) and Hawaiian baby wood rose (*Argyreia nervosa*), *Acacia confusa, Acacia obtusifolia, Acacia simplicifolia, Desmanthus Illinoensis*, or Cannabis (*Cannabis sativa, C. indica* and *C. ruderalis*).

Dosages

Toxicity and therapeutic efficacy of compounds described herein, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and thereby reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

In one embodiment, the pharmaceutical compositions described herein provide a dosage form of the pharmaceutical compositions described here for administration to a subject. In one embodiment, the subject is suffering from or has the symptoms of one or more neurologic diseases or disorders or wishes to enhance one or more cognitive or sensory motor traits. The dosage form can be administered, for example, to a subject, or a subject in need thereof. In one aspect, the subject is a mammal, or a mammal in need thereof. In one aspect, the subject is a human, or human in need thereof. In one aspect, the subject is a human or a human in need thereof. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (≥18 years of age).

One or more dosage forms of the compositions described herein can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to a neurological or neurodegenerative disease or disorder.

In one embodiment, the compositions described herein can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage.

Methods of Treatment

Methods for treating, prophylaxis of, or ameliorating symptoms of an infectious disease including administering an effective amount of the compositions detailed herein are contemplated. Methods for treating, prophylaxis of, or ameliorating symptoms of a bacterial or viral infection or modulating a bacterial or viral infection that includes administering an effective amount of an aqueous or solid extract of one or more of *Fomitopsis officinalis, Trametes versicolor*, and/or *Hericium erinaceus* are also contemplated. Another embodiment described herein is a method of treating a subject suffering from or having the symptoms of an infectious disease or disorder by orally administering a composition comprising *Fomitopsis officinalis, Trametes versicolor*, or *Hericium erinaceus*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers. Another embodiment described herein is a method of treating a subject suffering from or having the symptoms of an infectious disease or disorder by orally administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of an infectious disease. Further, provided herein are means for modulating an inflammatory response that includes administering to a subject an effective amount of the composition described herein.

In some embodiments, a dose of the composition may be administered to the subject 1 time per day, 2 times per day, 3 times per day, 4 times per day, or 5 times per day. In some embodiments, the dose includes at least 1 capsule, at least 2 capsules, at least 3 capsules, at least 4 capsules, at least 5 capsules, at least 6 capsules, at least 7 capsules, at least 8 capsules. In some embodiments, the composition may be administered to the subject for about 1 to 30 consecutive days, about 5 to 30 consecutive days, about 10 to 30 consecutive days, about 15 to 30 consecutive days, about 1 to 15 consecutive days, about 5 to 15 consecutive days, or about 10 to 15 consecutive days. In some embodiments, the composition may be administered to the subject for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

For example, administration of the composition to the subject may result in inhibition or slowing of the infectious disease. In another example, administration of the composition to the subject may result in inhibition or slowing of the normal rate of increase of viral load as compared to an untreated subject. As used herein, the term "viral load" is a measurement of the amount of a virus in a subject. In some embodiments, the infectious disease may cause lung inflammation. The lung inflammation may be associated with, but not limited to, respiratory failure, respiratory distress, pulmonary disease, cystic fibrosis, asthma, bronchitis, inflammation/swelling of the lungs, chronic obstructive pulmonary disease (COPD), pneumonia, restrictive lung disease, bronchiectasis, pulmonary fibrosis, sarcoidosis, allergies, smoking, emphysema, acute respiratory distress syndrome (ARDS), interstitial lung disease (ILD), pneumoconiosis or lung cancer. The lung diseases may affect the alveoli, trachea, interstitium, pluera, bronchi and/or bronchioles. The lung disease may cause diffuse alveolar damage, denuded alveolar lining cells with reactive type II pneumocyte hyperplasia, intra-alveolar fibrinous exudates, loose interstitial fibrosis, intra-alveolar loose fibrous plugs of organizing pneumonia, intra-alveolar organizing fibrin, damaged alveolar epithelial cells, desquamated cells within the alveolar space, cellular fibromyxoid exudates, desquamation of pneumocytes, hyaline membrane formation (e.g., indication of ARDS), pulmonary oedema, (e.g., early-phase ARDS). The lung disease may also cause chronic inflammation such as interstitial mononuclear inflammatory infiltrates dominated by lymphocytes. The lung disease may cause infiltration of the intra-alveolar spaces in the lung by multinucleated syncytial cells with atypical enlarged pneumocytes characterized by large nuclei, amphophilic granular cytoplasm, and/or prominent nucleoli that show viral cytopathic-like changes. The lung disease may cause increased inflammatory FCN1+ macrophages that replace FABP4+ macrophages in severe disease. The lung disease may cause highly expanded and functional competent tissue resident clonal CD8+ T cells in mild disease. Blood vessels or interstitial areas between alveoli may not be affected by the lung disease. In some embodiments, the infectious disease may include one or more symptoms such as shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure. In some embodiments, the subject may have COPD, cardiovascular disease, diabetes mellitus, hypertension, or a combination thereof. In some embodiments, the subject may be at least 1 year old, at least 2 years old, at least 3 years old, at least 4 years old, at least 5 years old, at least 6 years old, at least 7 years old, at least 8 years old, at least 9 years old, at least 10 years old, at least 11 years old, at least 12 years old, at least 13 years old, at least 14 years old, at least 15 years old, at least 16 years old, at least 17 years old, at least 18 years old, at least 19 years old, at least 20 years old, at least 21 years old, at least 22 years old, at least 23 years old, at least 24 years old, at least 25 years old, at least 26 years old, at least 27 years old, at least 28 years old, at least 29 years old, at least 30 years old, at least 31 years old, at least 32 years old, at least 33 years old, at least 34 years old, at least 35 years old, at least 36 years old, at least 37 years old, at least 38 years old, at least 39 years old, at least 40 years old, at least 41 years old, at least 42 years old, at least 43 years old, at least 44 years old, at least 45 years old, at least 46 years old, at least 47 years old, at least 48 years old, at least 49 years old, at least 50 years old, at least 51 years old, at least 52 years old, at least 53 years old, at least 54 years old, at least 55 years old, at least 56 years old, at least 57 years old, at least 58 years old, at least 59 years old, at least 60 years old, at least 61 years old, at least 62 years old, at least 63 years old, at least 64 years old, at least 65 years old, at least 66 years old, at least 67 years old, at least 68 years old, at least 69 years old, at least 70 years old, at least 71 years old, at least 72 years old, at least 73 years old, at least 74 years old, at least 75 years old, at least 76 years old, at least 77 years old, at least 78 years old, at least 79 years old, at least 80 years old, at least 81 years old, at least 82 years old, at least 83 years old, at least 84 years old, at least 85 years old, at least 86 years old, at least 87 years old, at least 88 years old, at least 89 years old, at least 90 years old, at least 91 years old, at least 92 years old, at least 93 years old, at least 94 years old, at least 95 years old, at least 96 years old, at least 97 years old, at least 98 years old, at least 99 years old, at least 100 years old, or even older.

In some embodiments, the infectious disease or condition may increase expression of growth factors. In some embodiments, the growth factors may be basic fibroblast growth factor and/or vascular endothelial growth factor. In some embodiments, the methods herein comprise administering a therapy for one of the symptoms or conditions associated with cytokine storm. For instance, if the subject develops coagulopathy, the method may comprise administering cryoprecipitate. In some embodiments, if the subject develops cardiovascular dysfunction, the method may comprise administering vasoactive infusion support. In some embodiments, if the subject develops distributive shock, the method may comprise administering alpha-agonist therapy. In some embodiments, if the subject develops cardiomyopathy, the method may comprise administering milrinone therapy. In some embodiments, if the subject develops respiratory failure, the method may comprise performing mechanical ventilation (e.g., invasive mechanical ventilation or noninvasive mechanical ventilation). In some embodiments, if the subject develops shock, the method may comprise administering crystalloid and/or colloid fluids.

In the absence of prompt intervention, such as that provided herein, a cytokine storm can result in permanent lung damage and, in many cases, death. The end stage symptoms of the cytokine storm include but are not limited to hypotension, tachycardia, dyspnea, fever, ischemia or insufficient tissue perfusion, uncontrollable hemorrhage, severe metabolism dysregulation, and multisystem organ failure. Deaths from infectious diseases such as COVID-19, are not caused by the virus itself, but rather, the cytokine storm that causes uncontrollable hemorrhaging; severe metabolism dysregulation; hypotension; tachycardia; dyspnea; fever; ischemia or insufficient tissue perfusion; and multisystem organ failure.

Methods for treating, prophylaxis of, or ameliorating symptoms of any type of pain known in the art in a subject in need thereof including administering an effective amount of the compositions detailed herein are contemplated. In one aspect, the pain comprises one or more of pain associated with psychological conditions, pain associated with infections (e.g., bacterial or viral infections), abdominal pain, abnormal gastrointestinal motility pain, acute herpes zoster pain, acute inflammatory pain, acute intermittent pain, acute musculoskeletal pain, acute obstetric pain, acute pain, acute post-operative pain (e.g., bunionectomy pain; abdominoplasty pain; knee pain from a total knee replacement; hip pain from a total hip replacement; pain from a laminectomy; pain from a hernia repair; or hemorrhoid removal pain), acute tendonitis pain, acute visceral pain, adiposis dolorosa pain, amyotrophic lateral sclerosis pain, angina-induced pain, anti-retroviral therapy induced neuralgia, anxiety pain, appendicitis pain, arrhythmia pain, arthritis pain, ataxia pain, back pain, Behcet's disease pain, bipolar disorder pain, bladder and urogenital disease pain, bone pain, brachial plexus avulsion injury pain, breakthrough pain, burn pain, burning mouth syndrome pain, bursitis pain, cancer chemotherapy induced neuralgia, cancer pain, cardiac arrhythmia pain, cardiac pain, carpal tunnel syndrome pain, central pain, cerebral ischemia, Cesarean-section pain, Charcot-Marie Tooth neuropathic pain, chemotherapy induced neuropathic pain, chest pain, cholecystitis pain, chronic and acute headache pain, chronic and acute neuropathic pain, chronic arthritis, chronic pain, chronic visceral pain, cluster headache pain, cold pain, complex regional pain syndrome, Crohn's disease pain, dental pain (e.g., third molar extraction), depression pain, diabetic neuralgia, diabetic neuropathic pain, diabetic peripheral neuropathic pain, drug therapy induced neuralgia, ectopic proximal and distal discharge pain, endometriosis pain, epilepsy pain, erythromelalgia pain, exercise induced angina pain, exercise induced pain, exercise pain, Fabry's disease pain, femur cancer pain, fibromyalgia pain, general neuralgias, granuloma annulare pain, Guillain-Barre pain, gut pain, Haglund syndrome pain, head pain, headache pain, hereditary sensory neuropathic pain, hernia pain, herpetic neuralgia pain, HIV-associated neuropathic pain, HIV-associated sensory neuropathic pain, hyperactivity bladder pain, hypertension pain, idiopathic pain, idiopathic sensory neuropathic pain, idiopathic small-fiber neuropathic pain, incontinence pain, inflammatory bowel disease pain, inflammatory pain, injury pain, interstitial cystitis (IC) pain, intestinal obstruction pain, intractable pain, irritable bowel syndrome pain, joint pain, labor pain, leprosy pain, lipoidica pain, malignancy pain, mechanical low back pain, migraine pain, Morton's neuroma pain, movement disorder pain, multiple sclerosis (MS) pain, musculoskeletal pain, myofascial pain syndrome pain, myotonia pain, neck pain, necrobiosis pain, nerve avulsion injury pain, nerve entrapment injury pain, neurodegenerative disorder pain, neuroendocrine disorder pain, neuropathic low back pain, neuropathic pain, nociceptive pain, non-malignant chronic bone pain, orofacial pain, osteoarthritis pain, painful bladder syndrome, painful legs, painful moving toes, painful neuromas, palpitations, pancreatic pain, paroxysmal extreme pain, pathological cough pain, pelvic pain, peripheral nerve injury pain, phantom pain, phlebitic pain, post spinal cord injury pain, post-amputation pain, post-herpetic neuralgia, post-mastectomy pain, post-stroke pain, postsurgical pain, premenstrual pain, prostatitis pain, pruritis pain, psychiatric disorder associated pain, pyelonephritis pain, radicular pain, radiculopathy, radiotherapy-induced neuropathic pain, renal colic pain, rheumatoid arthritis pain, sarcoidosis pain, sciatica pain, severe pain, shingles pain, sickle cell anemia pain, sinusitis pain, spinal cord injury pain, spinal stenosis pain, sports injury pain, stress-induced angina pain, stress-induced pain, stroke pain, temporomandibular joint pain, tendonitis pain, tension headache pain, thalamic pain, tinnitus pain, trauma pain, traumatic brain injury pain, traumatic neuroma, trigeminal autonomic cephalalgia, trigeminal neuralgia, urinary incontinence pain, visceral pain, widespread pain, or other types of pain.

Methods for treating, prophylaxis of, or ameliorating symptoms of any type of pain known in the art in a subject in need thereof that includes administering an effective amount of an aqueous or solid extract of one or more of *Agaricus brasiliensis* f. *blazei*, *Cordyceps militaris*, *Flammulina velutipes*, *Fomes fomentarius*, *Fomitopsis officinalis*, *Ganoderma applanatum*, *Ganoderma lucidum Ganoderma oregonense Grifola frondosa*, *Hericium erinaceus*, *Inonotus obliquus*, *Lentinula edodes*, *Phellinus linteus*, *Piptoporus betulinus*, *Pleurotus ostreatus*, *Schizophyllum commune*, and/or *Trametes versicolor* are also contemplated. Another embodiment described herein is a method of treating a subject suffering from or having the symptoms of any type of pain known in the art by orally administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of any type of pain known in the art.

Methods of Use

Another embodiment is a method of treating or preventing an infectious disease or disorder in a subject in need thereof, the method comprising administering to the subject a therapeutically effective amount of an extract, a compound, or formulation disclosed herein. Another embodiment is a method of treating or lessening the severity of any type of pain known in the art in a subject in need thereof, the method comprising administering to the subject a therapeutically effective amount of an extract, a compound, or formulation disclosed herein.

Another embodiment is a composition comprising *Fomitopsis officinalis* and *Trametes versicolor*, extracts thereof, compounds isolated therefrom, or pharmaceutically acceptable salts, hydrates, solvates, prodrugs, stereoisomers, or tautomers thereof, or combinations thereof, and optionally one or more pharmaceutically acceptable carriers, for use in treating an infectious disease or disorder in a subject in need thereof. Another embodiment is a composition comprising *Fomitopsis officinalis* and *Trametes versicolor*, extracts thereof, compounds isolated therefrom, or pharmaceutically acceptable salts, hydrates, solvates, prodrugs, stereoisomers, or tautomers thereof, or combinations thereof, and optionally one or more pharmaceutically acceptable carriers, for use in treating or lessening the severity of any type of pain in a subject in need thereof.

Another embodiment is a composition comprising *Fomitopsis officinalis, Trametes versicolor*, or *Hericium erinaceus*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers, for use in treating an infectious disease or disorder in a subject in need thereof. Another embodiment is a composition comprising *Fomitopsis officinalis*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers, for use in treating an infectious disease or disorder in a subject in need thereof. Another embodiment is a composition comprising *Fomitopsis officinalis, Trametes versicolor*, or *Hericium erinaceus*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers, for use in treating or lessening the severity of any type of pain in a subject in need thereof. Another embodiment is a composition comprising *Fomitopsis officinalis*, extracts thereof, compounds isolated therefrom, or a pharmaceutically acceptable salts, hydrates, solvates, prodrugs, stereoisomers, or tautomers thereof, or combinations thereof, and optionally one or more pharmaceutically acceptable carriers, for use in treating or lessening the severity of any type of pain in a subject in need thereof.

Another embodiment is a composition comprising *Trametes versicolor*, extracts thereof, compounds isolated therefrom, or pharmaceutically acceptable salts, hydrates, solvates, prodrugs, stereoisomers, or tautomers thereof, or combinations thereof, and optionally one or more pharmaceutically acceptable carriers, for use in treating an infectious disease or disorder in a subject in need thereof. Another embodiment is a composition comprising *Trametes versicolor*, extracts thereof, compounds isolated therefrom, or pharmaceutically acceptable salts, hydrates, solvates, prodrugs, stereoisomers, or tautomers thereof, or combinations thereof, and optionally one or more pharmaceutically acceptable carriers, for use in treating or lessening the severity of any type of pain in a subject in need thereof.

Another embodiment is a composition comprising *Fomitopsis officinalis* and/or *Trametes versicolor*, extracts thereof, or compounds isolated therefrom, for use in treating an infectious disease in a subject in need thereof. Another embodiment is a composition comprising *Fomitopsis officinalis* and/or *Trametes versicolor*, extracts thereof, or compounds isolated therefrom, for use in treating or lessening the severity of any type of pain in a subject in need thereof.

Another embodiment is a composition comprising *Fomitopsis officinalis, Trametes versicolor*, and/or *Hericium erinaceus*, extracts thereof, compounds isolated therefrom, for use in treating an infectious disease in a subject in need thereof. Another embodiment is the use of a composition comprising *Fomitopsis officinalis* and/or *Trametes versicolor* in the manufacture of a medicament for treating an infectious disease or disorder. Another embodiment is a composition comprising *Fomitopsis officinalis, Trametes versicolor*, and/or *Hericium erinaceus*, extracts thereof, compounds isolated therefrom, for use in treating an infectious disease in a subject in need thereof. Another embodiment is the use of a composition comprising *Fomitopsis officinalis* and/or *Trametes versicolor* in the manufacture of a medicament for treating or lessening the severity of any type of pain.

Another embodiment is the use of a pharmaceutical composition comprising *Fomitopsis officinalis* and/or *Trametes versicolor* extracts thereof, or compounds isolated therefrom and optionally a pharmaceutically acceptable carrier, in the manufacture of a medicament for treating an infectious disease in a subject in need thereof. Another embodiment is the use of a pharmaceutical composition comprising *Fomitopsis officinalis* and/or *Trametes versicolor* extracts thereof, or compounds isolated therefrom and optionally a pharmaceutically acceptable carrier, in the manufacture of a medicament for treating or lessening the severity of any type of pain in a subject in need thereof.

Another embodiment is the use of a pharmaceutical composition comprising *Fomitopsis officinalis, Trametes versicolor* and/or *Hericium erinaceus* extracts thereof, or compounds isolated therefrom and optionally a pharmaceutically acceptable carrier, in the manufacture of a medicament for treating an infectious disease in a subject in need thereof. Another embodiment is the use of a pharmaceutical composition comprising *Fomitopsis officinalis, Trametes versicolor* and/or *Hericium erinaceus* extracts thereof, or compounds isolated therefrom and optionally a pharmaceutically acceptable carrier, in the manufacture of a medicament for treating or lessening the severity of any type of pain in a subject in need thereof.

Another embodiment is a use of a composition comprising *Fomitopsis officinalis* and/or *Trametes versicolor*, extracts thereof, compounds isolated therefrom, or pharmaceutically acceptable salts, hydrates, solvates, prodrugs, stereoisomers, or tautomers thereof, combinations thereof in the manufacture of a medicament for treating or preventing an infectious disease or disorder in a subject in need thereof. Another embodiment is a use of a composition comprising *Fomitopsis officinalis* and/or *Trametes versicolor*, extracts thereof, compounds isolated therefrom, or pharmaceutically acceptable salts, hydrates, solvates, prodrugs, stereoisomers, or tautomers thereof, combinations thereof in the manufacture of a medicament for treating or lessening the severity of any type of pain in a subject in need thereof.

Another embodiment is a use of a composition comprising *Fomitopsis officinalis, Trametes versicolor*, and/or *Hericium erinaceus*, extracts thereof, compounds isolated therefrom, or pharmaceutically acceptable salts, hydrates, solvates, prodrugs, stereoisomers, or tautomers thereof, combinations thereof in the manufacture of a medicament for treating or preventing an infectious disease or disorder in a subject in need thereof. Another embodiment is a use of a composition comprising *Fomitopsis officinalis, Trametes versicolor*, and/or *Hericium erinaceus*, extracts thereof, compounds isolated therefrom, or pharmaceutically acceptable salts, hydrates, solvates, prodrugs, stereoisomers, or tautomers thereof, combinations thereof in the manufacture of a medicament for treating or lessening the severity of any type of pain in a subject in need thereof.

Another embodiment is a method for treating or preventing an infectious disease or disorder in a subject in need thereof comprising administering a composition comprising *Fomitopsis officinalis* and/or *Trametes versicolor*, extracts thereof, compounds isolated therefrom, or pharmaceutically acceptable salts, hydrates, solvates, prodrugs, stereoisomers, or tautomers thereof, or combinations thereof to the subject. Another embodiment is a method for treating or lessening the severity of any type of pain in a subject in need thereof comprising administering a composition comprising *Fomitopsis officinalis* and/or *Trametes versicolor*, extracts thereof, compounds isolated therefrom, or pharmaceutically acceptable salts, hydrates, solvates, prodrugs, stereoisomers, or tautomers thereof, or combinations thereof to the subject.

Another embodiment is a method for treating or preventing an infectious disease or disorder in a subject in need thereof comprising administering a composition comprising *Fomitopsis officinalis, Trametes versicolor*, and/or *Hericium erinaceus* extracts thereof, compounds isolated therefrom, or pharmaceutically acceptable salts, hydrates, solvates, prodrugs, stereoisomers, or tautomers thereof, or combinations thereof to the subject. Another embodiment is a method for treating or lessening the severity of any type of pain in a subject in need thereof comprising administering a composition comprising *Fomitopsis officinalis, Trametes versicolor*, and/or *Hericium erinaceus* extracts thereof, compounds isolated therefrom, or pharmaceutically acceptable salts, hydrates, solvates, prodrugs, stereoisomers, or tautomers thereof, or combinations thereof to the subject.

Methods of Manufacturing

In an embodiment, is a method of manufacturing a composition comprising *Fomitopsis officinalis, Trametes versicolor*, and/or *Hericium erinaceus*, extracts thereof, compounds isolated therefrom, or pharmaceutically acceptable salts, hydrates, solvates, prodrugs, stereoisomers, or tautomers thereof, combinations thereof. The method may include growing a mushroom on a substrate, separating the mushroom mycelium from a fruitbody and the substrate, incubating the mycelium with a solvent, forming a solution, extracting an aqueous fraction from the solution, extracting a solid fraction from the solution. The substrate may be one or more of rice, oat, straw, or sawdust. The mushroom may be grown on a substrate at about 15° C. to about 30° C. for about 20 to about 120 days, at about 10° C. to about 40° C. for about 10 to about 100 days, at about 20° C. to about 30° C. for about 15 to about 60 days, or at about 15° C. to about 30° C. for about 1 to about 100 days, at about 15° C. to about 30° C. for about 30 to about 50 days, at about 20° C. to about 30° C. for about 30 to about 50 days. The mushroom may be grown on a substrate at about 20° C. to about 25° C. for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days, about 100 days, about 101 days, about 102 days, about 103 days, about 104 days, about 105 days, about 106 days, about 107 days, about 108 days, about 109 days, about 110 days, about 111 days, about 112 days, about 113 days, about 114 days, about 115 days, about 116 days, about 117 days, about 118 days, about 119 days, or about 120 days. In some embodiments, the solvent is cold water.

The mycelium as described herein may be flash frozen at about −18° C. The frozen mycelium may be freeze-dried and ground into a powder. The mycelium may be freeze-dried at a pressure of about 500 mbar to about 3,000 mbar, about 1,000 mbar to about 3,000 mbar, about 1,000 mbar to about 2,000 mbar, about 1,500 mbar to about 2,000 mbar, or about 1,500 mbar to about 3,000 mbar. Heat of about 60° C. to 100° C., about 65° C. to 100° C., about 70° C. to 100° C., about 75° C. to 100° C., about 75° C. to 95° C., about 75° C. to 90° C., about 75° C. to 85° C., or about 75° C. to 80° C. may be applied to the mycelium. The freezer-dried mycelium may be milled to a fineness of about 50 microns to about 1,000 microns, about 100 microns to about 1,000 microns, about 150 microns to about 1,000 microns, about 160 microns to about 1,000 microns, about 170 microns to about 1,000 microns, about 180 microns to about 1,000 microns, about 190 microns to about 1,000 microns, about 200 microns to about 1,000 microns, about 500 microns to about 1,000 microns, about 50 microns to about 950 microns, about 100 microns to about 950 microns, about 150 microns to about 950 microns, about 160 microns to about 950 microns, about 170 microns to about 950 microns, about 180 microns to about 950 microns, about 190 microns to about 950 microns, about 200 microns to about 950 microns, about 500 microns to about 950 microns, about 50 microns to about 900 microns, about 100 microns to about 900 microns, about 150 microns to about 900 microns, about 160 microns to about 900 microns, about 170 microns to about 900 microns, about 180 microns to about 900 microns, about 190 microns to about 900 microns, about 200 microns to about 900 microns, about 500 microns to about 900 microns, about 50 microns to about 850 microns, about 100 microns to about 850 microns, about 150 microns to about 850 microns, about 160 microns to about 850 microns, about 170 microns to about 850 microns, about 180 microns to about 850 microns, about 190 microns to about 850 microns, about 200 microns to about 850 microns, about 500 microns to about 850 microns, about 50 microns to about 800 microns, about 100 microns to about 800 microns, about 150 microns to about 800 microns, about 160 microns to about 800 microns, about 170 microns to about 800 microns, about 180 microns to about 800 microns, about 190 microns to about 800 microns, about 200 microns to about 800 microns, about 500 microns to about 800 microns, about 50 microns to about 750 microns, about 100 microns to about 750 microns, about 150 microns to about 750 microns, about 160 microns to about 750 microns, about 170 microns to about 750 microns, about 180 microns to about 750 microns, about 190 microns to about 750 microns, about 200 microns to about 750 microns, about 500 microns to about 750 microns, about 50 microns to about 500 microns, about 100 microns to about 500 microns, about 150 microns to about 500 microns, about 160 microns to about 500 microns, about 170 microns to about 500 microns, about 180 microns to about 500 microns, about 190 microns to about 500 microns, about 200 microns to about 500 microns, about 500 microns to about 600 microns. The mycelium may be milled using a 20-80 standard mesh. The milled mycelium can be filled into capsules, made into tablets, tinctures, or further used as a base for a medicinal product effective as an antimicrobial and/or for potentiating a host mediated response.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Immune Stimulation

Aqueous, ethanol, and solid fractions of FO were tested for their impact on pro- and anti-inflammatory cytokine and chemokine activity in human peripheral blood mononuclear cells (PBMCs). Notably, the aqueous fraction of FO produced a robust upregulation of 19 out of 22 cytokines assayed, while the solid fraction produced a nearly similar effect, inducing activity of all 22 tested cytokines (FIG. 1). The strongest effects were observed on IL-1β, IL-6, MCP-1, MIP1α, MIP1β, ranging from approximately 8,000 to 145,000-fold increases.

Figure 3:
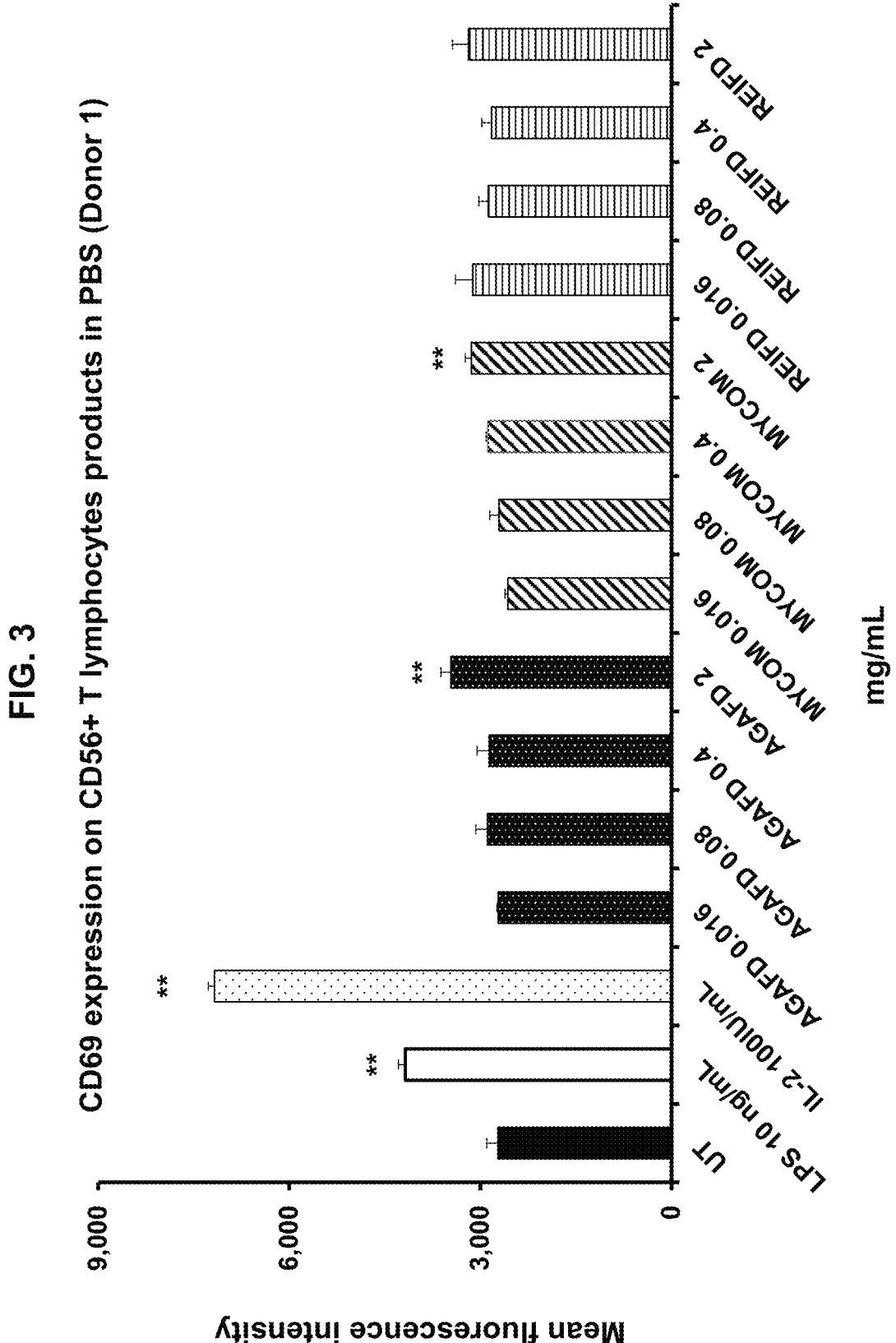
FIG. 3 shows CD69 expression on NKT cells in 24-hour whole blood cultures treated with products prepared in PBS (Donor 1). The LPS and IL-2 controls (tested at a single dose) are plotted for comparison. Statistical significance is indicated on the bar graph (* $p < 0.05$, ** $p < 0.01$). Abbreviations: Agarikon freeze dried (AGAFD), MyCommunity (MYCOM), Reishi freeze dried (REIFD).
Figure 4:
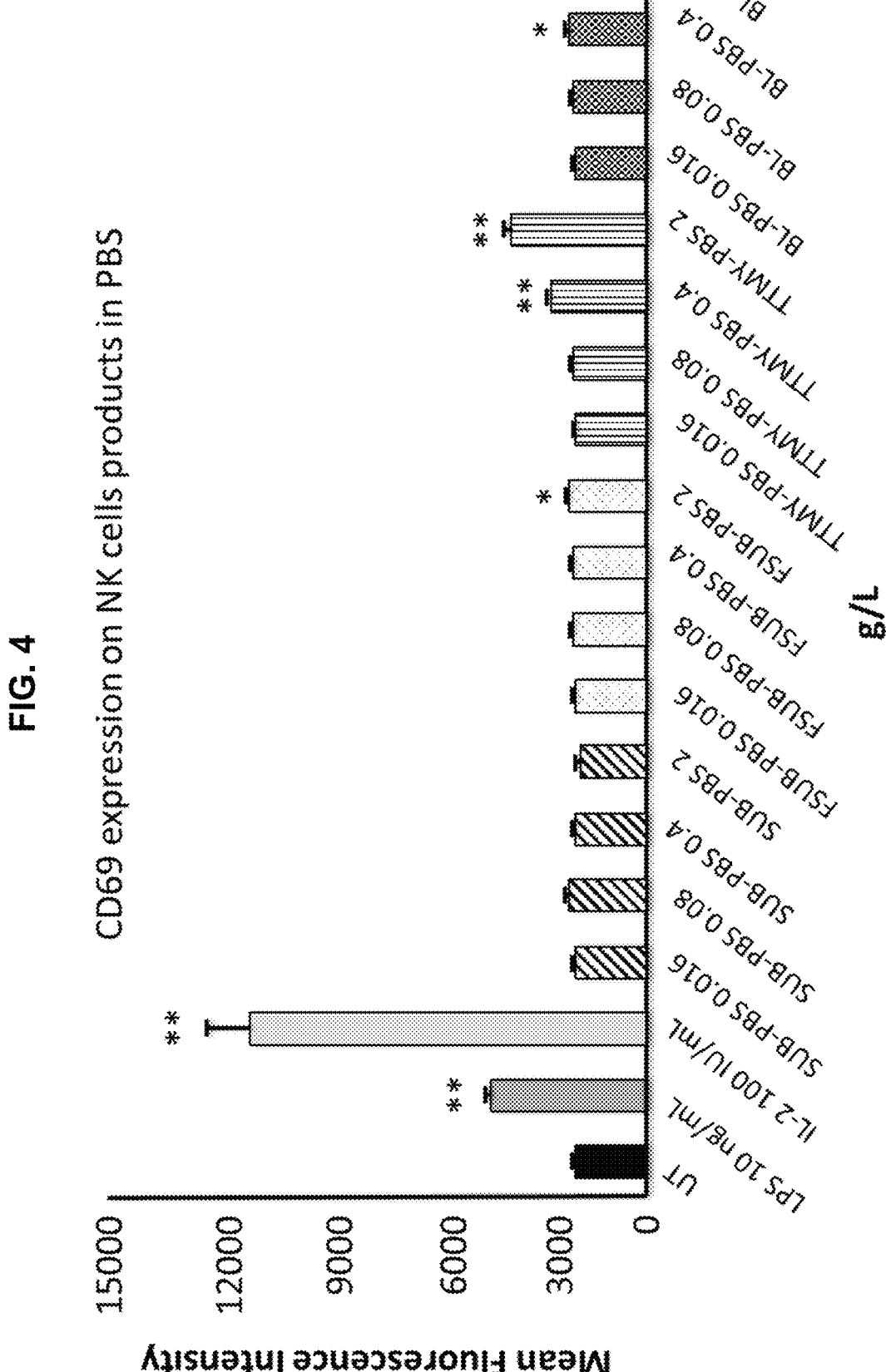
FIG. 4 shows CD69 expression on NK cells in 24-hour peripheral blood mononuclear cell cultures treated with products prepared in PBS. The LPS and IL-2 controls (tested at a single dose) are plotted for comparison. Statistical significance is indicated on the bar graph (* $p < 0.05$, ** $p < 0.01$). The positive control IL-2 has been removed from the line graph to better show the differences between products. Abbreviations: Substrate (SUB), Fermented Substrate (FSUB), Turkey Tail Mycelium (TTMY), Blend (BL).
Figure 5:
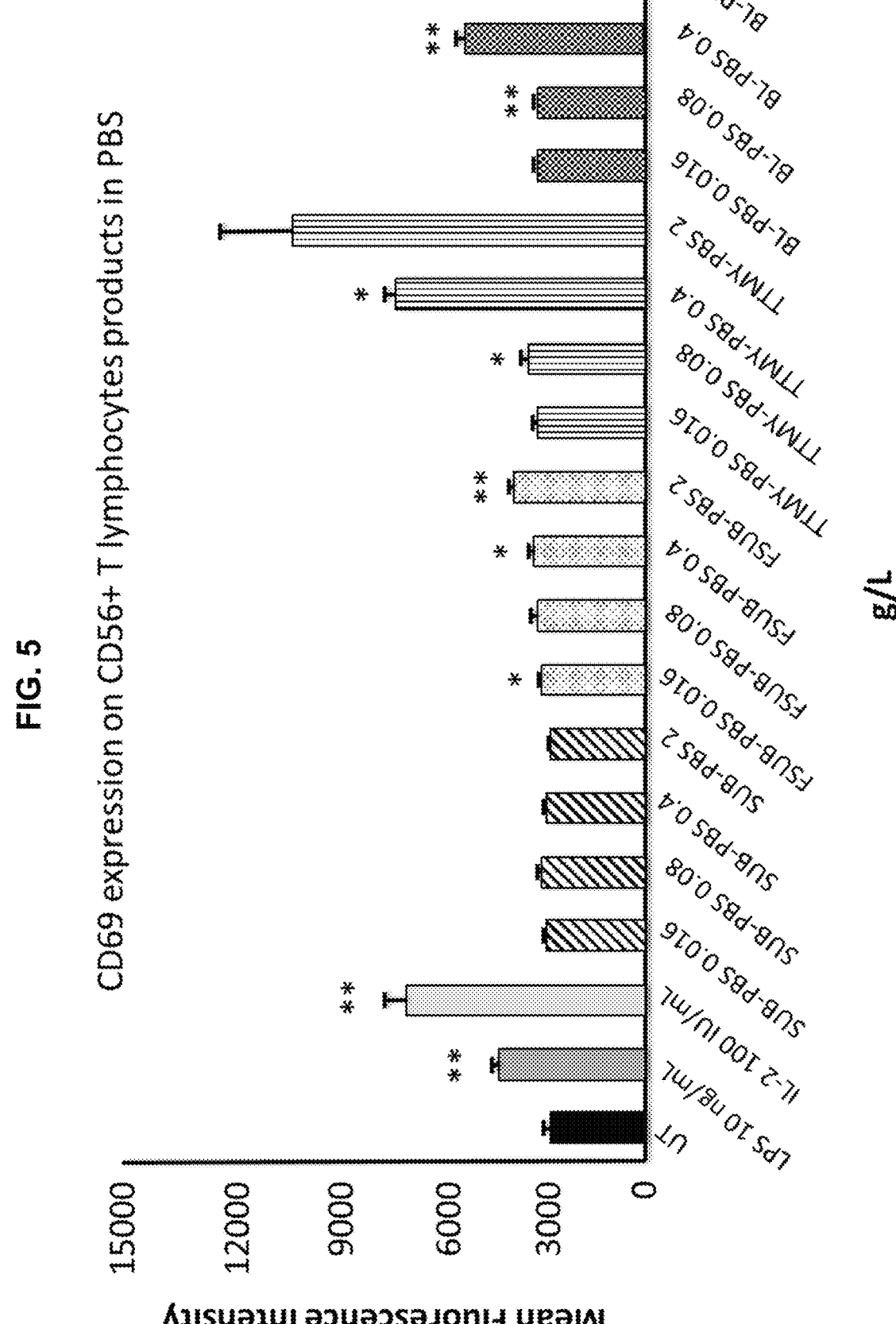
FIG. 5 shows CD69 expression on NKT cells in 24-hour peripheral blood mononuclear cell cultures treated with products prepared in PBS. The LPS and IL-2 controls (tested at a single dose) are plotted for comparison. Statistical significance is indicated on the bar graph (* $p < 0.05$, ** $p < 0.01$). Abbreviations: Substrate (SUB), Fermented Substrate (FSUB), Turkey Tail Mycelium (TTMY), Blend (BL).

The immune activation marker CD69 was investigated to determine the impact of F. *officinalis* extracts on T lymphocytes (FIG. 2), natural killer T (NKT) cells (FIG. 3), and natural killer (NK) cells (FIG. 4). Aqueous-soluble fractions of *F. officinalis* were able to activate these cell types in PBMCs. The immune activation marker CD69 was investigated to determine the impact of substrate, fermented substrate, and Turkey Tail mycelium on natural killer T (NKT) cells (FIG. 5).

Antioxidant Activity

Figure 6A:
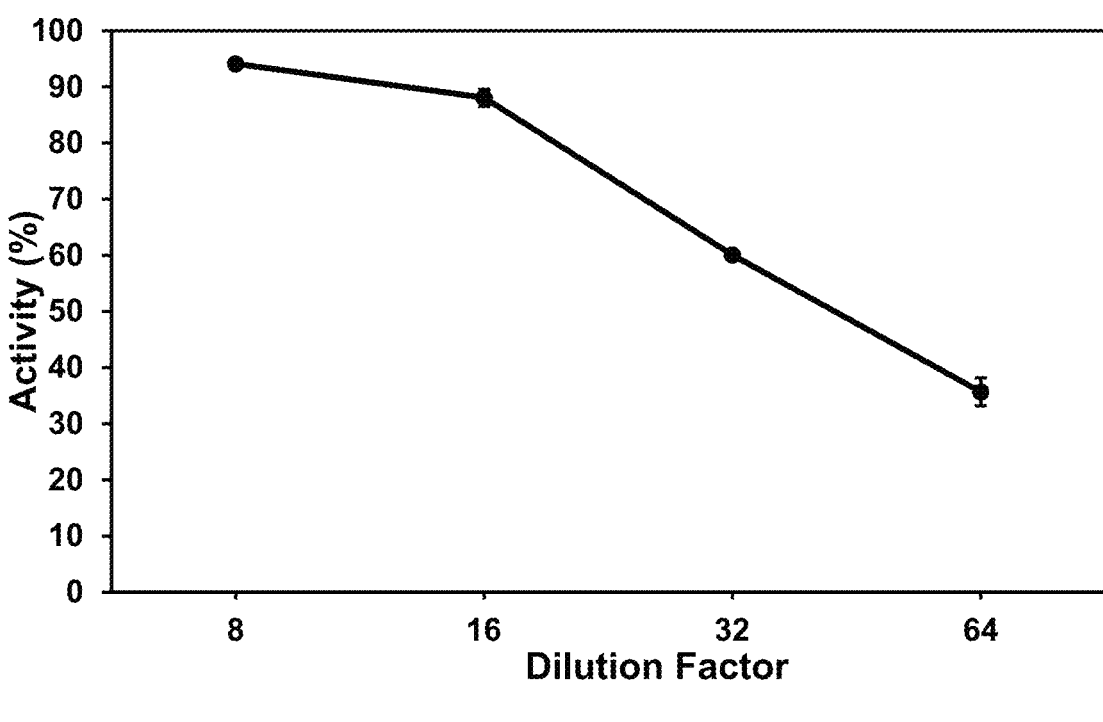
FIG. 6A-B show iron (Fe) metal chelating activity of FO extract (FIG. 6A) and nitric oxide (NO) antioxidant activity assay for FO extract (FIG. 6B).
Figure 6B:
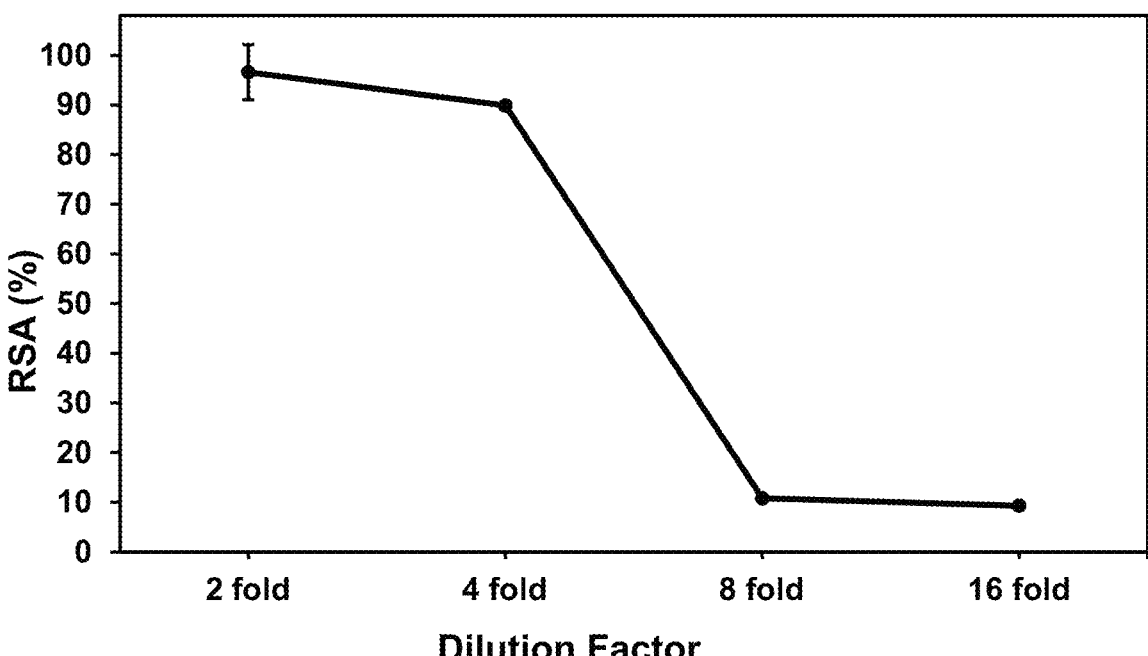
Figure 7A:
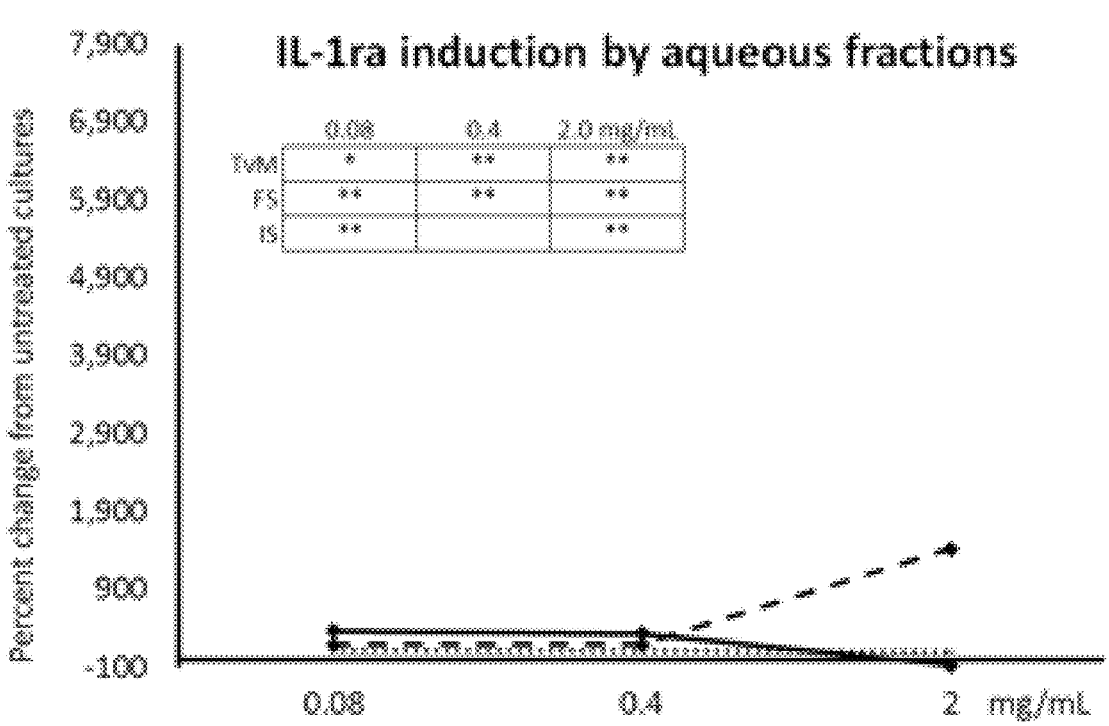
FIG. 7A-D show the changes in levels of the cytokines Interleukin-1 receptor antagonist (IL-1ra) and Interleukin-10 in supernatants from human PBMC cultures. The PBMC were cultured for 24 h in the presence of serial dilutions of *Trametes versicolor* mycelium (TvM), fermented substrate (FS), or initial substrate (IS). The effects on IL-1ra and IL-10, both involved in anti-inflammatory processes as part of the resolution of inflammatory processes, of aqueous extracts are shown in FIG. 7A and FIG. 7C, and of the solid fractions are shown in FIG. 7B and FIG. 7D. Data are shown for three doses (0.08, 0.4, and 2 mg/mL), where the doses represent the amount of starting material used to produce a given fraction. Data are presented as mean±standard deviation of the percent change seen in triplicate cultures and represents one of three separate experiments using PBMC cells from three different healthy human donors. Inserted tables: Statistical significance is indicated as * for P<0.05 and ** for P<0.01.
Figure 7B:
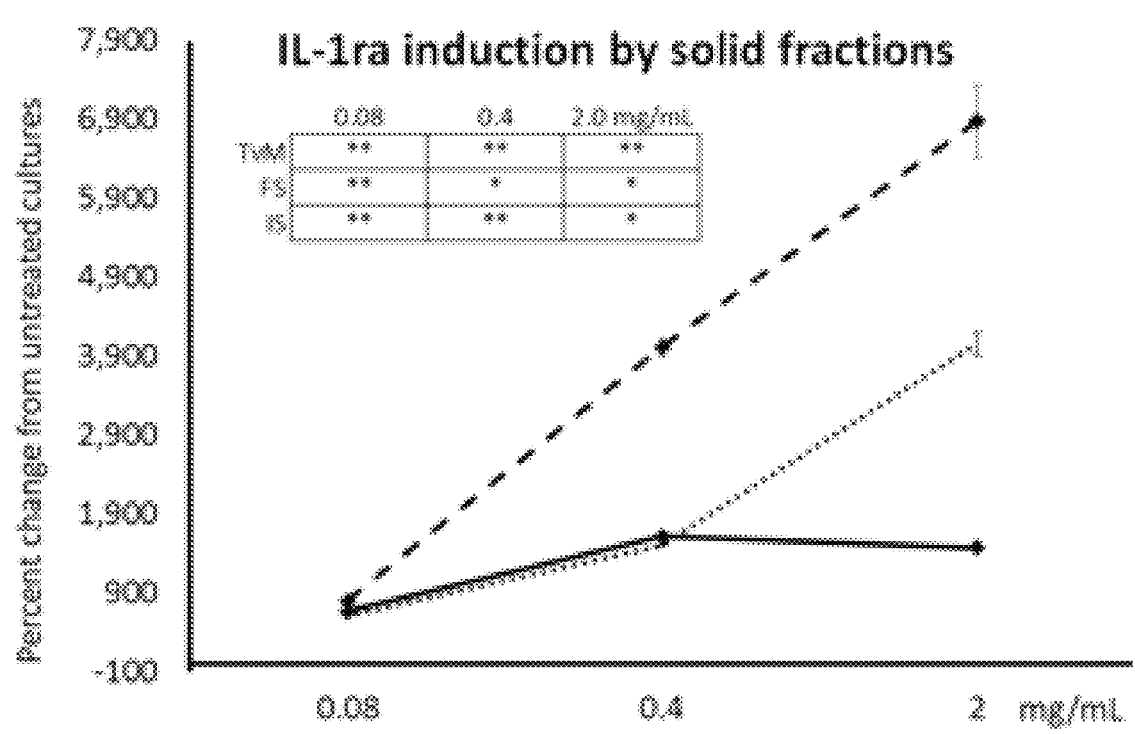
Figure 7C:
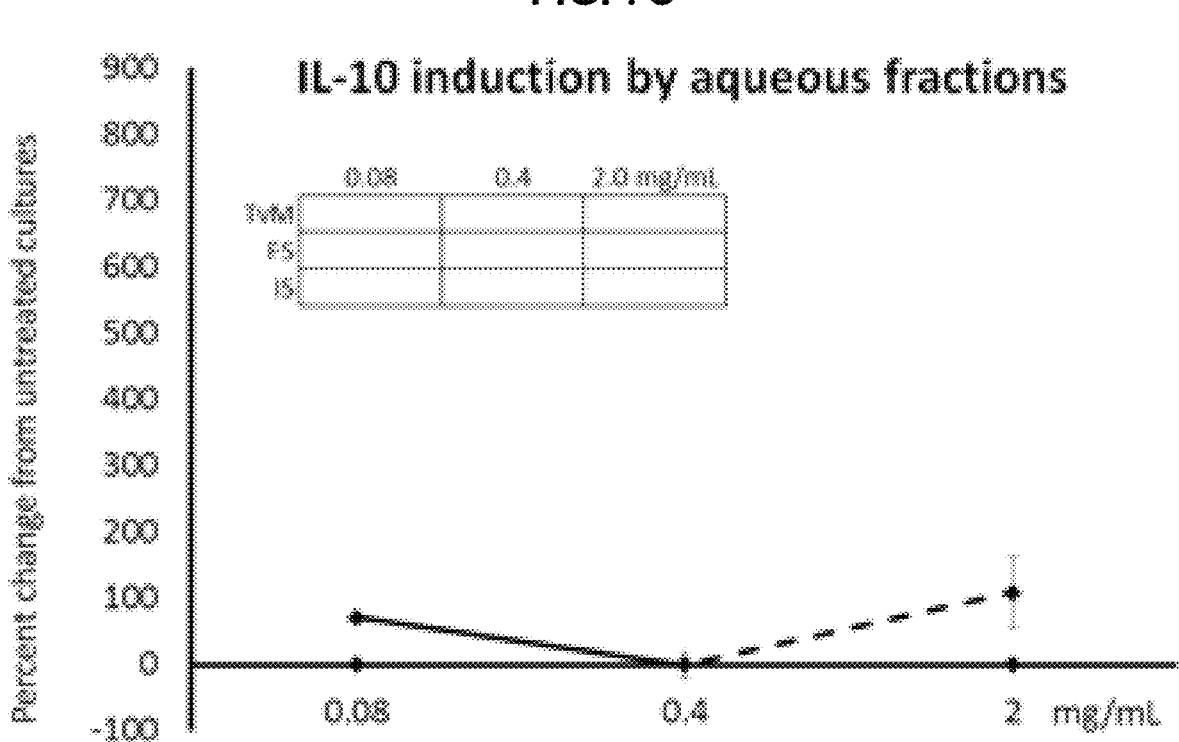
Figure 7D:
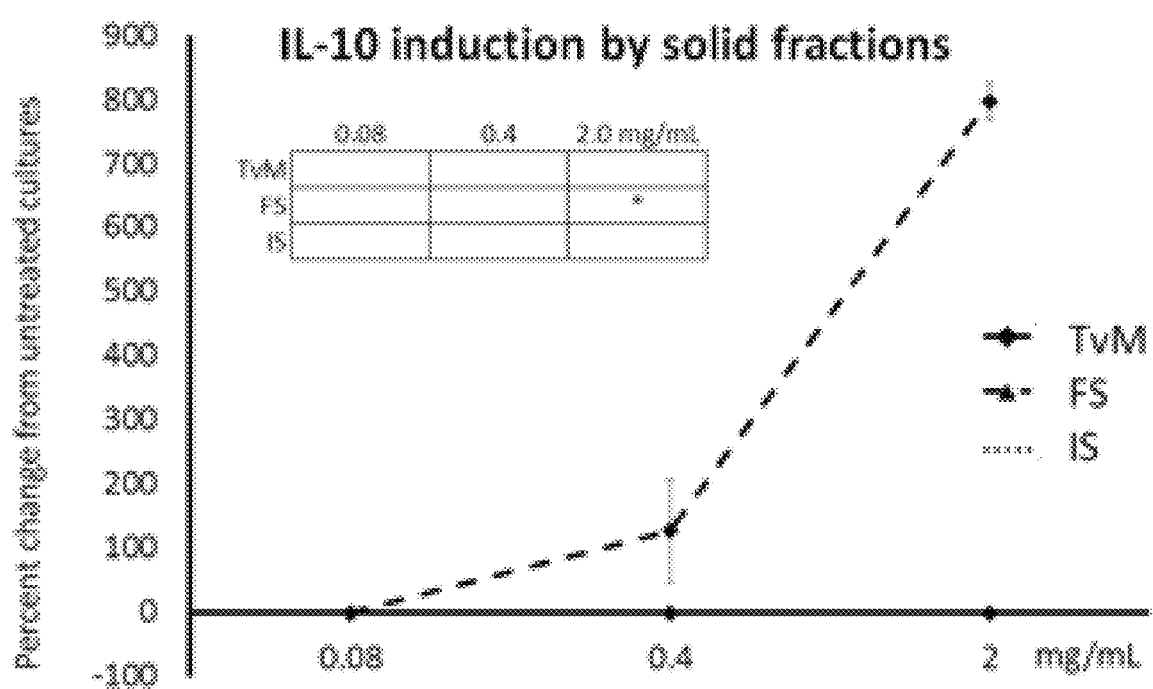

FO extracts were evaluated by DPPH and nitric oxide assays to determine in vitro and ex vivo antioxidant activity. Preliminarily, DPPH assays were performed on FO-VI extracts to determine in vitro antioxidant activity. Early tests showed high percentages of radical scavenging activity, and therefore extracts were tested in the ex vivo nitric oxide test. FO-VI extracts were found to have high NO scavenging activity at 2-fold and 4-fold dilutions of a standard hydroethanolic extract of FO-VI grown on rice (FIG. 6B). This activity was not detected at an 8-fold dilution of the initial extract, or any further dilution. FO-VI also showed significant $Fe^{2+}$ chelating ability (FIG. 6A). FO-VI extract showed chelation ability at ~90% activity at 8- and 16-fold dilutions, then decreased linearly to ~35% activity at 64-fold dilution.

Genomics

Eleven strains of *F. officinalis* were sequenced, and fungal barcoding data generated from this study were uploaded to NCBI GenBank as PopSet #194476224, including strains: F01, F04, F05, F06, F08, F09, F10, F11, F12, F13, and F14 (SEQ ID NOs. 1-13). As is standard in fungal species identification, the highly polymorphic, non-coding internal transcribed spacer (ITS) regions of nuclear ribosomal DNA were targeted for sequencing.

A comparison of the ITS1 and ITS2 regions between strains revealed that 3 out of the 11 strains have unique genetic mutations in these regions that differentiate them from the majority of strains submitted. Whereas most of the strains shared identical sequences in the ITS1 fungal barcoding region, F10-Hoh had the most divergent/unique sequence, including a heterozygous G/C read at position 133, as well as a two-nucleotide insertion that was absent in every other strain sequenced. Both F10 and F08 share a heterozygous G/T at positions 70 and 81, respectively, whereas all other strains are homozygous for T. The F08 strain is also heterozygous at position 67 with both G/T where all other strains have a G. The ITS2 region was nearly identical for all strains investigated, although F05 has a unique SNP at position 99.

Strains 'East Tyrol,' 'MPVW,' and 'Larson's Meadow' were sequenced, "Accugenix FunITS" analysis positively identified these strains as *F. officinalis*. At least four more strains 'Bagby Hot Springs,' 'Nowak', 'Larson's Meadow II,' and 'Saltsprings Island BC' were sequenced and confirmed to be strains of *F. officinalis*.

Although the SNPs that were identified do not lead to any functional differences in medicinal activity, they do indicate genetic divergence among these strains. The more these ITS regions differ, the more likely it is we find other forms of genetic variability (e.g., genes underlying synthesis of bioactive compounds). Despite most *F. officinalis* strains in the Fungi Perfecti culture library being cloned from conks growing in the Pacific Northwest, this small exploratory dataset has already confirmed genetic diversity among these populations. By sequencing the same fungal barcoding region for the remaining 49 strains, the strains will be assessed on a population genetic level and determine if there are distinct clades associated with geographic regions. If a subset of strains needs to be selected for testing, this understanding can be used to submit samples with a greater degree of genetic diversity and be more likely to capture outliers. This fungal barcoding strategy is simple and inexpensive relative to other sequencing methodologies and would serve as a good starting point for future analyses, considering these strains also exhibit significant variation in antiviral activity.

Cultivation

FO-VI is currently utilized as the production strain, cultivated on organic brown rice in Unicorn SABs. Growth is enhanced with oat hull fiber supplementation. FO-VI grows better in Unicorn SABs than SACO2 bags.

Future research will adopt genomic approaches to further understand FO metabolism and possibilities for subsequent growth enhancement. Comprehensive strain comparisons will also take place to catalog immunological, antiviral, and antibacterial properties across the strain library. Analytical approaches like LC/MS and NMR can be leveraged to discover the bioactive components in the mycelium organism. Additionally, the components can be separated (mycelium and fermented substrate) and tested in an effort to identify causative elements therein.

All these approaches aim to address the high immunological activity of FO and how this activity can be enhanced. This line of research has several applications: zoonotic viruses with pandemic potential, avian and swine influenza, coronaviruses, infections of livestock importance, enteric necrosis—broiler chickens, oncoviruses, EBV, HPV, stealth pathogens, and/or *borrelia*.

Example 2

We have shown that solid fractions of rice substrate colonized by *Trametes versicolor* upregulate expression of cytokines with known anti-inflammatory effects, including IL-10 and IL-1ra. We also showed that *Fomitopsis officinalis* products strongly induce IL-10 and IL-1ra expression in vitro. IL-1ra inhibits the pro-inflammatory effect of IL-1β (Dinarello and van der Meer, Seminars in Immunology 25(6): 469-484 (2013)), a pro-inflammatory cytokine that contributes to the development of ARDS like that found in COVID-19 patients, suggesting that these fungal products could confer beneficial immunomodulatory effects on those infected by SARS-CoV-2.

Interestingly, oral consumption of freeze-dried mycelial powder of *Trametes versicolor* (TvM) has also been shown to increase abundance of CD8+ T cells in humans. Torkelson et al., *ISRN Oncology* 1-7 (2012). When compared to healthy controls, patients infected with SARS-CoV-2 showed significantly reduced abundance of CD8+ T cells and NK cells. Zheng et al., *Cellular & Molecular Immunology* (2020). Retrospective analysis of 522 patients in two Wuhan hospitals confirmed that low counts of T-cells (including CD8+) were associated with mortality. Diao et al., Reduction and Functional Exhaustion of T Cells in Patients with Coronavirus Disease 2019, 2020). A case study of a non-severe COVID-19 patient revealed that immune cells including CD8+ T cells were recruited during the illness and persisted for at least a week after recovering from symptoms. Theverajan et al., *Nature Medicine* (2020). Functional exhaustion of these cytotoxic lymphocytes has been associated with severe SARS-CoV-2 virus infection, implying antiviral immunity may break down during early onset of COVID-19 in patients who become critically ill. Zheng et al., *Cellular & Molecular Immunology* (2020).

A phase I human clinical study from Bastyr University evaluated the impact of TvM on post-chemotherapy recovery among breast cancer patients. Generally, chemotherapy elicits a reduction in lymphocyte counts and a corresponding reduction in the activity of natural killer (NK) cells as well as cytotoxic CD8+ T cells and B lymphocyte antigen CD19+ cells. Reductions in these cell types decrease immune system activity, and similarly other work found that patients with SARS-CoV-2 infection tend to have reduced numbers of NK and CD8+ T cells. Zheng et al., *Cellular & Molecular Immunology* (2020).

This phase I study identified Turkey tail as a safe post-radiation immunotherapy that may help offset immunodeficiencies. Oral doses of 6 and 9 g of Tv were found to increase recovery of lymphocyte counts and tumoricidal activity of NK cells. Further, TvM increased counts of CD19+ cells and CD8+ T cells (P=0.0003). In addition to influencing tumoricidal activity, cytotoxic T cells are also involved with cellular response to pathogens including viruses and bacteria. Cytotoxic T cells often recruit cytokines such as TNF-α and IFN-γ to combat pathogens, suggesting that Turkey tail likely provides immune benefits beyond the context of post-radiotherapy recovery.

The mycelium of *Trametes versicolor* (Turkey tail) mushroom and its fermented substrate each show potent and complementary immune activating properties in vitro (FIG. 7A-FIG. 7D). This study investigated the impact of aqueous and solid fractions of initial substrate (IS), fermented substrate (FS), Tv mycelium (TvM), and a FS-TvM blend on immune system potentiation. The early immune response marker CD69 in several subsets of immune cells was targeted. CD69 plays a major role in NK cytotoxicity of target cells and is rapidly induced in NK cells during immune cell activation. In human lymphocytes, TvM produced a robust increase in CD69 and natural killer T cells and also activated T cells and NK cells.

Human peripheral blood mononuclear cells (PBMCs) were treated with Turkey tail to determine the impact on inflammatory cytokines. Notably, Tv induced the production of two anti-viral cytokines, interferon-gamma (IFN-γ) and macrophage inflammatory protein-1α (MIP-1α). Additionally, Tv also induced the expression of two key anti-inflammatory cytokines, interleukin-1-receptor antagonist (IL-1ra) and interleukin-10 (IL-10) (FIG. 7A-FIG. 7D). Tv also induced strong expression of granulocyte colony-stimulating factor (G-CSF) and interleukin-8 (IL-8), two biomarkers that influence stem cell regeneration. Subsequent unpublished in-house analysis of NIS cytokine data was conducted to facilitate visualization of general trends (FIG. 8).

Notably, the FS produced a strong, unique profile for cytokine activation that stood out among the tested treatments. The strong activity of the aqueous TvM fraction demonstrated that Tv efficacy is attributed to much more than the classically identified insoluble beta-glucans. Ultimately, the data provide a basis for immune activity of TvM and FS through a multifaceted impact on NK cells, anti-inflammatory cytokines, and regenerative cytokines.

Example 3

The biological activity of isolated compounds from *Fomitopsis officinalis* were studied using a Vaccinia virus assay. Frozen Fo ricelium samples were macerated in 95% Ethyl alcohol in a 1:1 (w/w) ratio for ~24 hours at which time the material was pressed and filtered through an 80-mesh screen. The resulting filtrate was passed through a 0.2-micron syringe prior to testing. Samples were received from Southern Research Institute-Frederick at 5 mL each and were stored at 4° C. Extract/original sample contained about 65% EtOH/H₂O. Another sample was received at 10 mL and stored at <4° C. The sample contained about 60-75% EtOH fungal extract. Samples were tested as % solutions, with the original submittal designated 100%. A 1:5 dilution was prepared of this stock in MEM with 2% FBS and 125 μL added to triplicate wells of previously seeded HFF cells. Subsequent 1:5 dilutions were performed using the Biomek liquid handling system for a total of 6 concentrations at 20, 4, 0.8, 0.16, 0.032 and 0.0064%. After addition of virus dilutions or medium for toxicity controls, the final dilutions of sample were 10, 2, 0.4, 0.08, 0.016 and 0.0032%. Ethanol percentages ranged from 6.0 to 7.5% at the top dilutions. Tests were performed to determine the effect of ethanol concentration on HFF cells and it was found that CC50 values of 7% were seen when testing a final 10% EtOH concentration in MEM with 2% FBS as determined by neutral red uptake. The antiviral drug Cidofovir was used as standard. Results are expressed as % viral inhibition rate in the Vaccinia assay in Table 2.

TABLE 2

| Compound | Concentration | Viral Inhibition Rate |
|---|---|---|
| Eburicoic | 100 μg/mL | 55% |
| Acid | 33 μg/mL | 29% |
| | 11 μg/mL | 27% |
| Dehydrosulphurenic | 33 μg/mL | 58% |
| Acid | 11 μg/mL | 16% |
| Sulphurenic acid | 33 μg/mL | 58% |
| | 11 μg/mL | 51% |
| | 3.7 μg/mL | 36% |
| Cidofovir | 1.67 μg/mL | 53% |
| | 0.56 μg/mL | 11% |

*Inonotus obliquus* extract (Chaga) was tested against SARS-CoV. Results are shown in Table 3.

with MAPKs that influence inflammation and neurological health using a previously described protocol (Fabian et al.,

TABLE 3

| Cmpd Name | Vehicle | Cell Line | Drug Units | Control Units | EC50-VISUAL-CONFIRMATORY | IC50-VISUAL-CONFIRMATORY | SI-VISUAL-CONFIRMATORY |
|---|---|---|---|---|---|---|---|
| 167512 | DMSO | Vero 76 | ng/ml | IU | 0.06 | >0.6 | >10 |

| Cmpd Name | POSITIVE EC50-VISUAL-CONFIRMATORY | POSITIVE IC50-VISUAL-CONFIRMATORY | POSITIVE SI-VISUAL-CONFIRMATORY | EC90-VY | SI-VY | POSITIVE EC90-VY | POSITIVE SI-VY |
|---|---|---|---|---|---|---|---|
| 167512 | 20 | >32000 | >1600 | 0.008 | >75 | <10 | >3200 |

TABLE 4

| Cmpd Name | Virus | Virus Strain | Assay | Vehicle | Cell Line | Drug Units | EC50 | IC50 | SI | CTRL Cmpd | CTRL Units | CTRL EC50 | CTRL IC50 | CTRL SI |
|---|---|---|---|---|---|---|---|---|---|---|---|---|---|---|
| He-II 25x | Flu A (H5N1) | Vietnam/ 1203/2004H | Neutral Red | DMSO | MDCK | µg/mL | 0.013 | >0.1 | >8 | Ribavirin | dilution | 7 | >320 | >46 |
| Hu 1x | Flu B | Malaysia/ 2506/2004 | Neutral Red | DMSO | MDCK | µg/mL | 0.024 | >0.05 | >2 | Ribavirin | dilution | 0.6 | >320 | >530 |
|  | Flu B | Malaysia/ 2506/2004 | Visual | DMSO | MDCK | µg/mL | 0.028 | >0.05 | >2 | Ribavirin | dilution | 0.6 | >320 | >530 |
|  | Flu B | Shanghai/ 361/02 | Neutral Red | DMSO | MDCK | µg/mL | 0.0072 | >0.05 | >7 | Ribavirin | dilution | 3 | >320 | >107 |
|  | Flu B | Shanghai/ 361/02 | Visual | DMSO | MDCK | µg/mL | 0.0038 | 0.05 | *15* | Ribavirin | dilution | 2 | >320 | >160 |
| HD Fraction 4 1x | Flu B | Malaysia/ 2506/2004 | Neutral Red | DMSO | MDCK | µg/mL | 0.031 | 0.061 | 2 | Ribavirin | µg/mL | 10 | >320 | >32 |
|  | Flu B | Malaysia/ 2506/2004 | Visual | DMSO | MDCK | µg/mL | 0.032 | >1 | >3 | Ribavirin | µg/mL | 3 | >320 | >107 |
|  | Flu B | Shanghai/ 361/02 | Neutral Red | DMSO | MDCK | µg/mL | 0.014 | >0.1 | >7 | Ribavirin | dilution | 7 | >320 | >46 |
| HDT5 1x | Flu A (H5N1) | Vietnam/ 1203/2004H | Neutral Red | DMSO | MDCK | µg/mL | 0.012 | >0.1 | *>8* | Ribavirin | dilution | 7 | >320 | >46 |
| Mycosoft 1x | Flu B | Shanghai/ 361/02 | Neutral Red | DMSO | MDCK | µg/mL | 0.028 | 0.043 | 2 | Ribavirin | dilution | 7 | >320 | >46 |

Underlined SI value indicates moderately active. Italicized SI values indicates slightly active.

Example 4

Agarikon (*Fomitopsis officinalis*, Fo) was found to interact with MAPK10/c-Jun N-terminal kinase 3 (JNK3), which influences several inflammatory cytokines including TNFα and IFN-γ as well as genes related to inflammation such as Tumor Necrosis Factor Receptor 1 (TNFR1), C-C Motif Chemokine 2 Precursor (CCL2), and Cyclooxygenase 2 (COX2) (de Lemos et al., *Molecular Neurobiology* (2018)). In addition, Fo was found to interact with two tropomyosin receptor kinases (TRKs), TrkA and TrkB, which function in the mammalian nervous system as receptors of nerve growth factor (NGF) and brain-derived neurotrophic factor (BDNF), respectively. The binding of NGF to TrkA broadly impacts TLR signaling and the NF-κB pathway, which provides downstream impacts on a multitude of inflammatory cytokines, including IL-1β, TNF-α, IL-6, and IL-8 as well as the anti-inflammatory cytokines IL-10 and IL-1RA (Prencipe et al., *Journal of Immunology* (2014)). Similarly, expression of TrkB is associated with the suppression of phospho-p38, which provides an anti-inflammatory effect on cytokines and proteins, such as TNF-α, IL-1β, IL-6, IL-18, iNOS, and COX-2 (Liang et al., *Experimental and Therapeutic Medicine* (2019)).

A scanELECT kinome profiling assay conducted by Eurofins DiscoverX corporation tested an ethyl acetate (EtOAc) fractions of agarikon (*Fomitopsis officinalis*, Fo) and lion's mane (*Hericium erinaceus*, He) for their ability to interact

Figure 9:
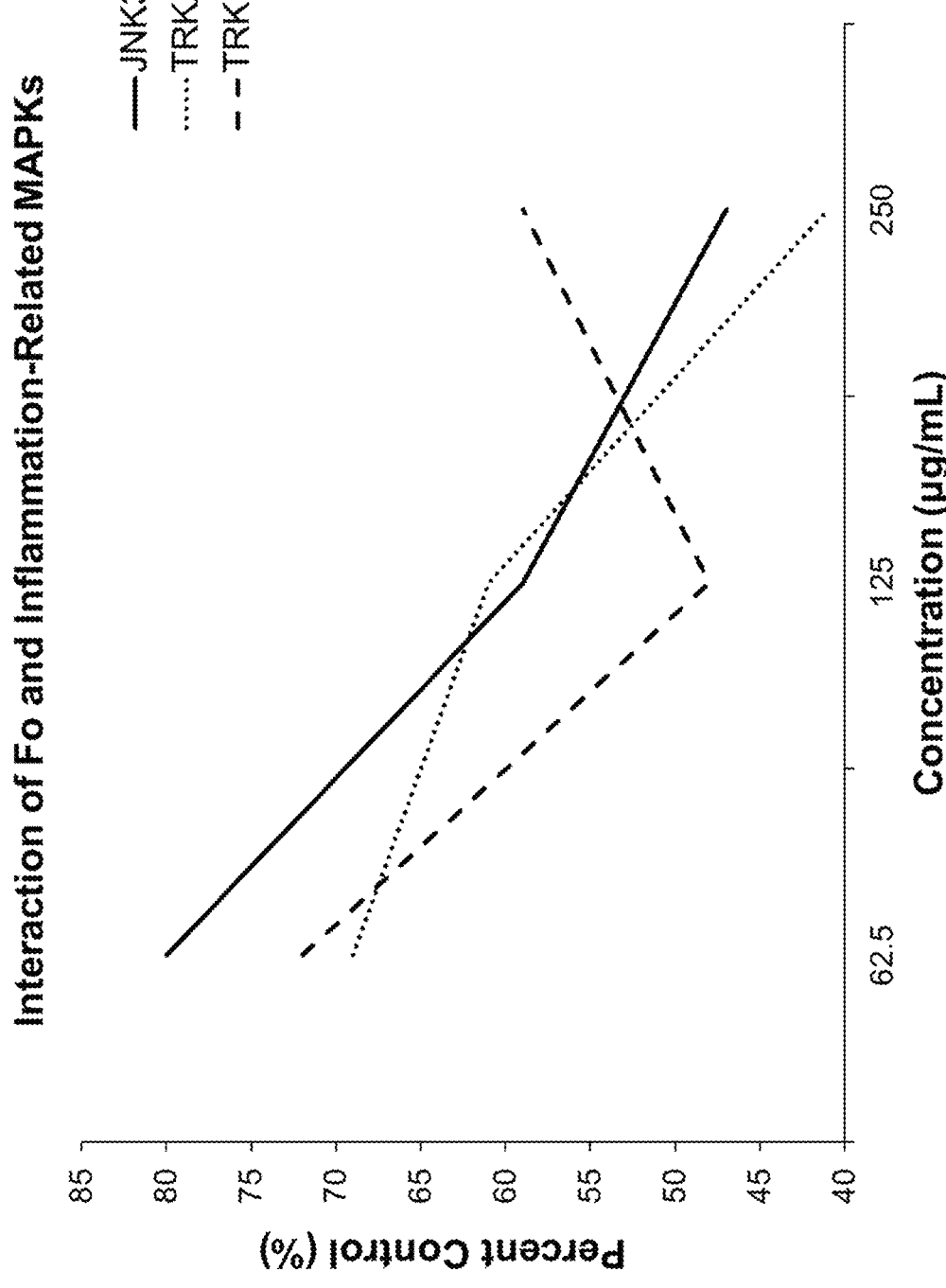
FIG. 9 shows the interaction of agarikon (*Fomitopsis officinalis*, Fo) and inflammation-related MAPKs. A scanELECT kinome profiling assay was used to analyze an ethyl acetate (EtOAc) fraction of Fo for its ability to interact with MAPKs that influence inflammation and neurological health. MAPK-Fo binding was compared to positive and negative controls, providing dissociation constants (Kd) to determine the level to which Fo prevents the kinase from binding to its respective ligand.
Figure 10:
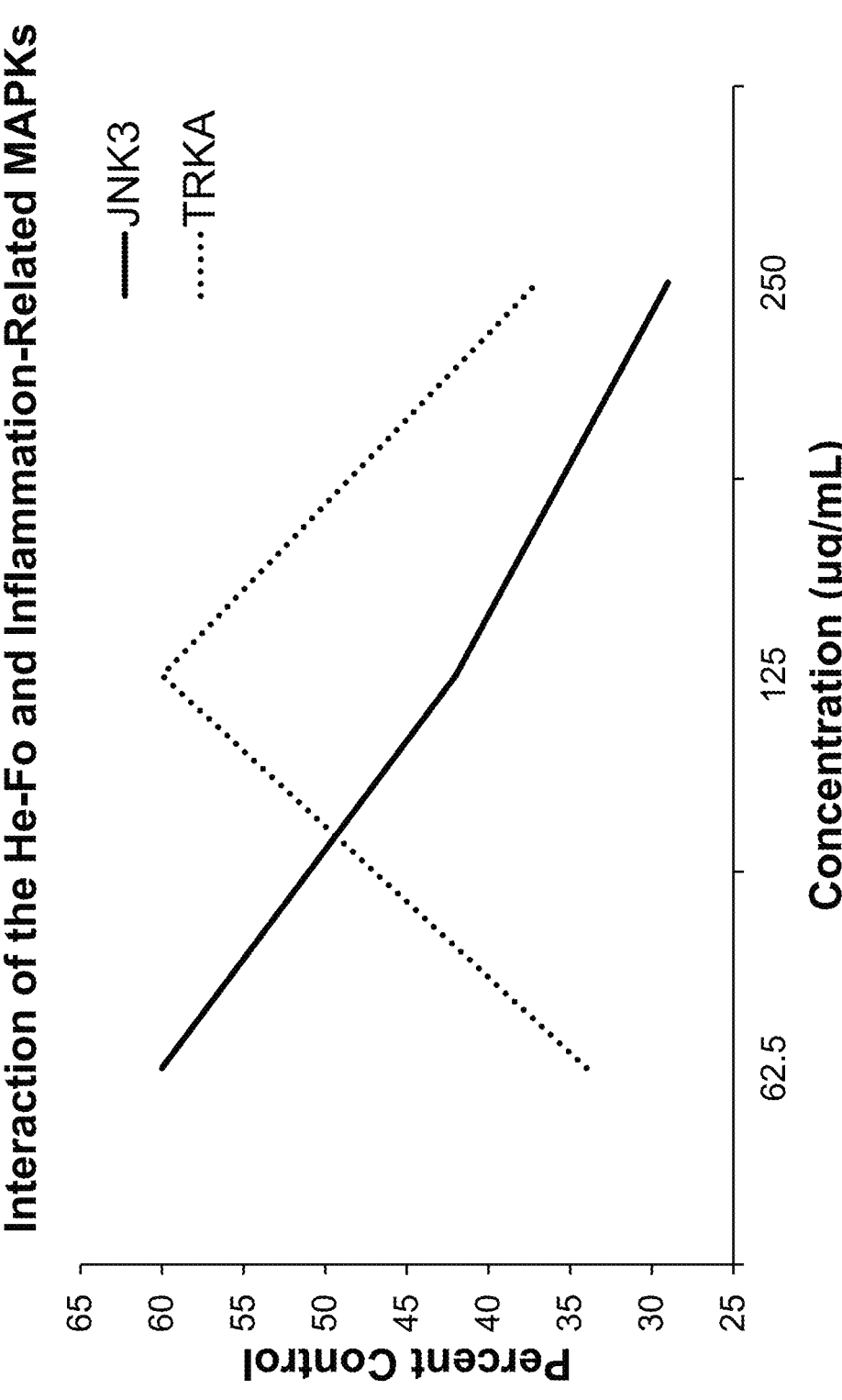
FIG. 10 shows the interaction of agarikon (*Fomitopsis officinalis*, Fo) and lion's mane (*Hericium erinaceus*, He) and inflammation-related MAPKs. A scanELECT kinome profiling assay was used to analyze an ethyl acetate (EtOAc) fractions of Fo and He for their ability to interact with MAPKs that influence inflammation and neurological health. MAPK-Fo binding was compared to positive and negative controls, providing dissociation constants (Kd) to determine the level to which Fo and He prevent the kinase from binding to its respective ligand.

*Nature Biotechnology* (2005)). Here, DNA-tagged human kinase isoforms were cultured and expressed in vitro. The scanELECT kinome profiling assay predominantly utilized *E. coli* as the cell line (strain BL21). Occasionally, a kidney cell line (HEK-293) was used. These cell lines were utilized to express human isoforms of the kinases of interest. The resulting cell lysates were used in a competitive binding assay in which they were incubated with Fo, He, or Fo-He mycelial extracts and tested by qPCR for the ability of the MAPKs in the cell lysates to bind to their respective ligands in the presence of the Fo, He, and Fo-He EtOAc fractions. MAPK binding was compared to positive and negative controls, providing dissociation constants (Kd) to determine the level to which Fo prevents the kinase from binding to its respective ligand (FIG. 9) and Fo-He prevents the kinase from binding to its respective ligand (FIG. 10). The negative control in these assays was a vehicle treatment of DMSO. The positive controls were kinase inhibitors that were varied by kinase: for JNK3 SB-203580, AST-487, and CEP-701 were used as positive controls; for JAK1 PKC-412, CGP-52421, and CEP-701 were used as positive controls; for TrkA and TrkB VX-680/MK-0457, Sunitinib, and CEP-701 were used as positive controls. The lower the percent control value, the stronger the binding affinity.

Fo and Fo-He were found to interact with JNK3, which influences several inflammatory cytokines including TNFα and IFN-γ as well as genes related to inflammation such as Tumor Necrosis Factor Receptor 1 (TNFR1), C-C Motif Chemokine 2 Precursor (CCL2), and Cyclooxygenase 2 (COX2) (de Lemos et al., *Molecular Neurobiology* (2018), 55(5), 4437-4452). In addition, Fo was also found to interact with two tropomyosin receptor kinases (TRKs), TrkA and TrkB, and Fo-He was found to interact with TrkA (FIGS. 9-10). TrkA and TrkB function in the mammalian nervous system as receptors of nerve growth factor (NGF) and brain-derived neurotrophic factor (BDNF), respectively. The binding of NGF to TrkA broadly impacts TLR signaling and the NF-κB pathway, which provides downstream impacts on a multitude of inflammatory cytokines, including IL-1β, TNF-α, IL-6, and IL-8 as well as the anti-inflammatory cytokines IL-10 and IL-1RA (Prencipe et al., *Journal of Immunology* (2014), 192(7), 3345-3354). Similarly, expression of TrkB is associated with the suppression of phospho-p38, which provides an anti-inflammatory effect on cytokines and proteins, such as TNF-α, IL-1β, IL-6, IL-18, iNOS, and COX-2 (Liang et al., *Experimental and Therapeutic Medicine* (2019), 17(3), 1688-1696). The Fo extract shows exceptional binding affinity for JNK3, TrkA and TrkB, and Fo-He shows exceptional binding affinity for JNK3 and TrkA (FIGS. 9-10). Therefore, the data demonstrates that Fo extracts and Fo-He stacked extracts modulate neuro-inflammatory signaling pathways.

Figure 11:
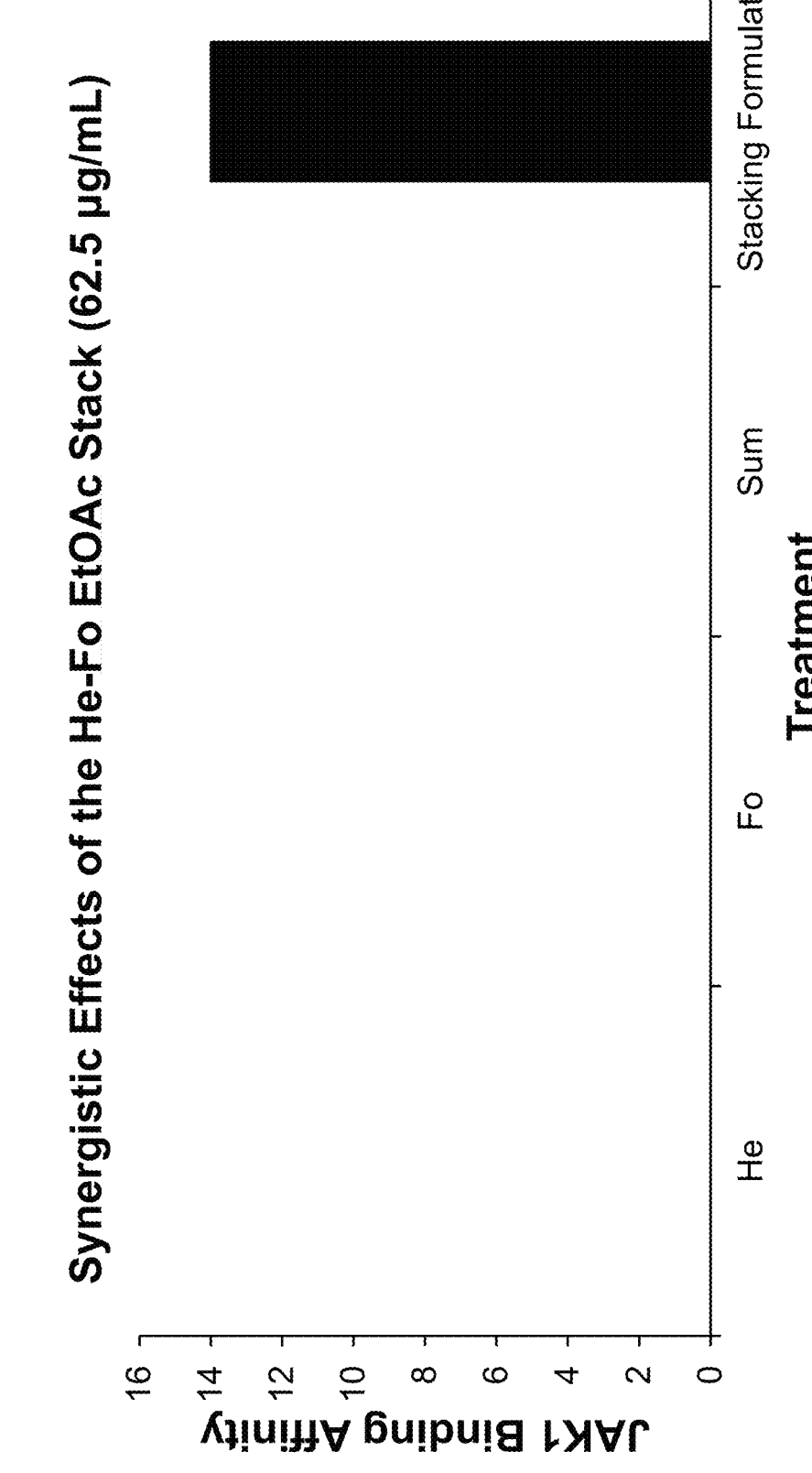
FIG. 11 shows the synergistic effects of He-Fo EtOAc stack. He and Fo alone lacked substantial binding affinity for Janus kinase 1 (JAK1), however, a Fo-He stack was found to interact with JAK1, suggesting a synergistic effect of the Fo-He stack formulation.

Interestingly, while He and Fo alone lacked substantial binding affinity for Janus kinase 1 (JAK1), a Fo-He stack was found to interact with this MAPK, suggesting a synergistic effect of the Fo-He stacking formulation (FIG. 11). JAK1 influences cytokine signaling, including IL-2, IL-4, IFN-α/β, IFN-γ, and IL-10, and it is implicated in brain aging and neurodegenerative diseases including AD.

Example 5

A 3-arm multi-center, randomized, double blinded, placebo-controlled clinical trial is conducted in two stages: (1) feasibility/safety, and (2) efficacy. The primary objective of the initial stage will be assessment of feasibility of the study protocol and safety of the medications. During the initial stage, 72 subjects (36 per site) will be enrolled at 2 sites (UC San Diego and UC Irvine). The study protocol will be implemented and feasibility and safety, as well as efficacy, data will be collected and analyzed. If feasibility and safety are demonstrated in this initial 72-subject sampling, the study will proceed to the second, larger stage involving UCSD, UCI, and UCLA (UCSF and UC Davis may also join) and recruitment of and intervention with the remainder of the 720 subjects will proceed. The study will be performed to evaluate the efficacy of Qing Fei Bai Du (QFPD), a blend of 21 herbs, and agarikon and Turkey tail (FoTv) immuno-supportive mushroom mycelium combination to prevent disease progression among high-risk patients with active COVID-19 who are assigned to outpatient management with home quarantine. They can each be utilized during the early stages of disease, where other pharmacologic options are absent. The primary objective of the larger second stage will be to compare the efficacy of (1) Chinese herbal medicine (QFPD) and (2) immune-supporting mushrooms (FoTv) to placebo in reducing the incidence of hospitalization due to COVID-19 among mildly-to-moderately symptomatic outpatients who have tested positive for COVID-19. High quality clinical trials are required to evaluate the safety and efficacy of each of these interventions for the prevention and treatment of COVID-19, and time is of the essence.

A secondary objective of the second stage of the study will be to further evaluate COVID-19 severity among subjects in each of the two medication arms, compared with placebo, as ascertained by duration of COVID-19 acute viral illness (as measured by fever and self-reported symptom scores), measures of cardiac enzymes, lymphocyte counts and other immune related biomarkers either on hospital admission (for hospitalized participants) or at end-of-study laboratory draw (for non-hospitalized participants), ICU admission due to COVID-19, intubation and ventilator therapy due to COVID-19, and death due to COVID-19. During the second stage, safety of the medications will also continue to be assessed through ongoing laboratory data collection either at the end of the intervention following the end of quarantine (for non-hospitalized patients) or utilizing hospital admission labs (for hospitalized patients).

The study will be open to patients who are mildly to moderately symptomatic and have tested positive for COVID-19 within the prior 48 hours. Participants will be randomized to one of three groups: Group 1—Chinese herbal medicine (QFPD); Group 2—Immune-supporting mushrooms (FoTv); Group 3—Inert placebo (encapsulated brown rice). It is anticipated that approximately 1200 potential candidates will be screened in order to arrive at the total number of study participants. 720 total study participants will be included in the study; 240 participants per arm. The study will be open to patients who have recently received a positive COVID-19 diagnosis and will be oversampled for patients who age above 60 years old. The focus on the initial 72 subjects will be on the feasibility and safety of the study however, the efficacy data will not be analyzed in the feasibility phase and will be analyzed in the efficacy part of the study.

Inclusion and Exclusion Criteria

Participants will be selected based on the following inclusion criteria: positive COVID-19 diagnosis made within the past 48 hours; able to demonstrate access to the following laboratory data: basic metabolic panel within the prior 1 year, complete blood count with differential within the prior 1 year, liver function test panel within the prior 1 year if abnormal, 3 years if within normal limits; age 21 years and older; women of childbearing potential (WOCBP) must have a negative urine or serum hCG; WOCBP must have a negative serum pregnancy test at screening and agree to use a double-barrier method of contraception throughout the study period; ability to understand informed consent in English and comply with all study procedures; either in person, by telephone or video; capable of answering online questions via daily email surveys; willing to avoid alcohol, *Cannabis* or dairy during the study period.

Participants will be excluded based on the following exclusion criteria: active hypoxia (defined by difficulty breathing or pressure on the chest) or other acute decompensation requiring hospitalization; current use of investigational agents to prevent or treat COVID-19; allergy to rice or to tree nuts; organ transplant status on immunosuppression; bleeding dyscrasia or on anticoagulation (aspirin and/or clopidogrel is allowed); known liver disease (ALT/AST>3×ULN or diagnosis of cirrhosis); known renal disease (eGFR<60 mL/min) or acute nephritis; pregnant or breastfeeding women; use of tolbutamide; use of systemic corticosteroids (hydrocortisone, cortisone, prednisolone, betamethasone, methylprednisolone, prednisone, dexamethasone), inhaled budesonide will be allowed; use of digoxin; use of oxacillin; use of Interferon; use of vincristine; use of cyclosporine; use of amiodarone; patients with a past medical history of epilepsy; use of monoamine oxidase inhibitors (MAOI).

Allowed concomitant medications are usual approved medications, as long as they are medically necessary and can be monitored safely during the study period. Prohibited concomitant medications include, as stated in the exclusionary criteria above, Tolbutamide, systemic corticosteroids (hydrocortisone, cortisone, prednisolone, betamethasone, methylprednisolone, prednisone, dexamethasone), digoxin, oxacillin, interferon, vincristine, cyclosporine, amiodarone, or monoamine oxidase inhibitors (MAOI). Further prohibited medications include, due to possible drug-drug interactions, the following: Ephedrine, pseudoephedrine, theophylline, aminophylline, caffeine, and monoamine oxidase inhibitors (MAOI). During this study, participants may not use other investigational agents with the intent to prevent SARS-CoV-2 infection.

Study participants with a baseline diagnosis of hypertension will be instructed to take daily blood pressure measurements using a home blood pressure cuff. They are to contact the study team with any measurement of systolic blood pressure above 150 or below 90, as well as diastolic measurements above 90. Study participants with a baseline diagnosis of diabetes mellitus who are on insulin or sulfonylureas will be instructed to take blood sugar measurements in the morning, as well as three times daily before meals. They are to notify the study team with any blood sugar reading below 70. Study participants with a baseline diagnosis of congestive heart failure or diuretic use will be required to monitor their weight daily and notify the study team if their weight changes by greater than 3 lbs (or 1.5 kg) throughout the 14-day trial period.

Test Product, Dose, Administration

Participants will be assigned to treatment groups using the following methodology. Following screening, study participants will be allocated in a random 1:1:1 distribution to each of the three study groups. Capsules containing placebo, QFPD, or FoTv will be placed in an identical appearing bottle to the other study medications. Following a 1:1:1 randomization, one of three investigative products will be assigned a sequential number. The treatment groups will be normalized by age group based on 5-year age bins.

The Host Defense mushroom product consists of equal numbers of Tv and Fo capsules. Each capsule contains 500 mg of either Tv or Fo freeze dried mycelium powder. The mycelium is cultivated on organic brown rice. The QFPD will be provided by SUN TEN Laboratories. A Certificate of Analysis (COA), including tests for heavy metals, aristolochic acid, and identification verification for each of the 21 herbs, will be provided with the batch commissioned for the study. The placebo will be prepared using the same organic grown rice and packaged into identical capsules containing 500 mg of rice. The inert placebo control will appear nearly identical to FoTV and to QFPD.

A dosage of 4 capsules each of agarikon and Turkey tail (FoTv) capsules (8 capsules total) will be taken three times daily (24 capsules daily), 30 minutes before and 60 minutes after meals, at morning, noon, and evening for 14 total consecutive days. Missed doses will be recorded in a daily treatment diary and remain unused. Should swallowing capsules be an issue, the capsules can be opened and dispensed into water for easy ingestion.

Participants will be on study drug or placebo for up to 30 days. Screening will be no longer than 48 hours after positive COVID-19 test. Treatment will be 14 days. Follow-up will be 14 days after start of treatment. The total duration of the study is expected to be 1 month. Eligible participants will receive a study treatment for up to 14 consecutive days unless hospitalized, in which case they are to stop study medication. Study participants who are not hospitalized yet remain febrile and report ongoing symptoms at EOT visit (Day 14) will continue all aspects of the EOT visit except for the blood draw. They will be contacted every 2-3 days by members of the study team until they are no longer symptomatic and are afebrile, consistent with CDC recommendations for removing quarantine, after which they will be directed to submit to outpatient laboratory blood draws.

All concomitant medication and concurrent therapies will be documented at Baseline/Screening Visit 1, Day 14 EOT visit, Day 28 Follow-up visit, and Day 58 end of study (EOS) visit. Dose, route, unit frequency of administration, and indication for administration and dates of medication will be captured. A targeted medical history, including history of current bleeding disorders, kidney disease, liver disease, immunocompromised status, and pregnancy/lactation status will be recorded at screening. Updated medical history including medication reconciliation and medication adverse effects, will be recorded at Baseline, Study Treatment Day 1 and 14, and at Study Day 28 and 58.

Efficacy Evaluations

The primary endpoint will be the incidence of severe COVID-19 as defined by being admitted to inpatient acute care for >24 hours for COVID-19 related illness. ER or other urgent evaluation without hospitalization is not included in this measure. The following will be measured: duration of COVID-19 acute viral illness as measured by fever and other symptom scores; ICU admission due to COVID-19; intubation due to COVID-19; death due to COVID-19.

The primary endpoints for the feasibility stage will be recruitment and completion rates. The primary endpoint for efficacy will be the incidence of hospitalization for COVID-19 related illness during the 14-day study period. Secondary endpoints are the following: safety and tolerability of FoTv given three times daily as determined by number of Grade 2 or greater clinical adverse effects; duration of fever other symptoms; incidence of ICU admission due to COVID-19; incidence of intubation due to COVID-19; incidence of death due to COVID-19; changes in cardiac enzymes, lymphocyte counts and other laboratory abnormalities either on hospital admission (for hospitalized participants) or at end-of-study laboratory draw (for non-hospitalized participants.

Statistics

Data management and statistical analysis will be performed using the Krupp Data System (KDS). The feasibility data will be analyzed using descriptive methods, Analysis of Variance (ANOVA) and Chi-square techniques. The comparability of the three treatment groups and study sites in baseline demographic and clinical features will be tested with ANOVA for continuous variables and Chi-square analyses for dichotomous variables. These variables will be added to the data analysis model, if we identify any significant differences at baseline between the groups.

A computer-generated randomization list will be prepared by the study biostatistician and will be used to randomize subjects into one of the three treatment groups with equal probability stratify by age (5 years bins). Randomization tables will be prepared at the beginning of the study and will be maintained by the study biostatistician.

Initially, descriptive statistics and exploratory graphing will be used to assess the normality and homogeneity of the data. If needed, the continuous outcome data will be transformed using an appropriate transformation (e.g., log transformation). Missing data will be examined to assess randomness and whether it is informative using methods developed by Diggle (1989). Missing data will be imputed, as appropriate. Similarly, it will be tested whether study drop-outs are random or systematic by comparing dropouts with study completers in terms of their baseline data. An absence of significant differences would support the random nature of dropouts. All statistical tests will be two-tailed. Differences will be considered statistically significant provided a p-value of 0.05 or less is obtained using SPSS version 25.

The primary study outcome is dichotomous (Y/N). For the incidence of hospitalization, Chi-Square tests will be employed to compare outcomes between each intervention and control subjects. With a sample size of 240 per group, the study will have 80% power to detect a difference in COVID-19 hospitalization between each of the intervention groups and the placebo control group of 20% vs 10% when using a two-tailed Chi-squared test. The secondary study outcomes are all dichotomous (Y/N) except for biometric data. For each dichotomous outcome, Chi-Square exact tests will be used to compare outcomes between each of the two intervention groups and the placebo control group. Continuous outcomes will be analyzed using a Mixed Effects model as described by Gibbons et al., *Psychopharmacology Bulletin* 24: 438-443 (1988), Hedeker et al., *Psychopharmacology Bulletin* 27: 73-77 (1991), and Laird et al., *Biometrics* 38(4): 963-974 (1982). This method allows the inclusion of subjects with missing data or those who were terminated early in the study, without relying on data imputation procedures. This method provides an estimate of the individual variability around the population trend, the variability of the individual intercepts (baseline values) and slopes (changes across time), and the correlation between them. Analyses will be conducted utilizing data from all randomized subjects for whom a baseline assessment and at least one post-baseline evaluation are available.

Rationale for number of participants: According to the WHO, 81% of COVID-19 cases are mild and 19% are likely to require hospitalization. By limiting the inclusion criteria to high-risk patients only, a larger rate of hospitalization for this population is anticipated. Based on a meta-analysis, case fatality rates are approximately four times higher among patients with cardiovascular disease (10.5%), diabetes (7.3%), chronic respiratory disease (6.3%) and hypertension (6.0%). As such, the hospitalization rate among this high-risk patient population is likely to be higher than 19%. Unfortunately, it is unclear from this or other reports how many of these patients would be enrolled in this study as opposed to presenting directly for hospitalization. Given the available information, it is reasonable to assume an elevated 30% rate of hospitalization among this study population.

Given this, the study will oversample older individuals (who are more likely to suffer from one or more comorbidities and for whom a higher rate of hospitalization is anticipated) at a level sufficient to ensure a minimum expected hospitalization rate of 20% in the study population as a whole. To achieve this, and also to further ensure equal allocation of age and age-related comorbidities across the 3 treatment arms, the study will employ a randomized block design (blocking on age, <60 vs. 60+). Based on an expected hospitalization rate of 20% in the placebo group, an effect size of 50% (i.e., a reduction from 20% to 10% in each of the active medication arms), and a significance level (alpha) of 0.05, a sample size of 199 per arm will be required to detect a difference in COVID-19 hospitalization rates between placebo and each of the treatment arms using a two-tailed Chi-square test with 80% study power (beta). An additional 20% (41 subjects per arm) will be added to protect against study dropout. Therefore, 240 individuals will be allocated to each of the three study arms (QFPD, FoTv, and placebo) for a total sample size, N, of 720. Given the limited clinical data on this specific indication for immune supporting mushrooms, the same sample size will be used in order to ensure a 1:1:1 group allocation. The initial 72 subjects (N=36 at the UCSD and UCI) will be part of the feasibility phase followed by data collection on the remaining 648 subjects.

The most significant potential benefit of this study is to contribute to the possible future availability of safe and inexpensive agents for the treatment of COVID-19. This study will generate important safety and efficacy data needed to evaluate the use of FoTv in time to provide guidance for the use of these medicines during the current pandemic. Furthermore, the collaborations formed as part of this study will provide a foundation for future studies evaluating the safety and efficacy of similar therapeutics for treatment of active COVID-19, such as varying treatments based on TCHM pattern diagnosis, the use of other mushroom compounds, and the application of these therapeutics for more severe manifestations of disease.

For the study participant, FoTv may provide direct benefit by potentially reducing the severity of their illness as measured by duration of fever, risk of hospitalization, intubation or death.

What is claimed is:

1. A method for treating, prophylaxis of, or ameliorating symptoms of an infectious disease in a subject in need thereof comprising:

administering to the subject a therapeutically effective amount of a composition comprising:

580-1,750 mg of an aqueous or solid fraction of *Fomitopsis officinalis* mycelium, a fermented substrate thereof, or a combination thereof; and 580-1,750 mg of an aqueous or solid fraction of *Trametes versicolor* mycelium, a fermented substrate thereof, or a combination thereof.

2. The method of claim 1, wherein the aqueous or solid fraction comprises beta-glucans.

3. The method of claim 1, wherein a dose of the composition is administered to the subject 3 times per day.

4. The method of claim 1, wherein the composition is in the form of a capsule.

5. The method of claim 3, wherein the dose comprises at least 4 capsules.

6. The method of claim 1, wherein the composition is administered to the subject for about 10 to 30 consecutive days.

7. The method of claim 1, wherein the composition is administered to the subject for about 14 days.

8. The method of claim 1, wherein the subject has COPD, Cardiovascular disease, diabetes mellitus, hypertension, or a combination thereof.

9. The method of claim 1, wherein the subject is at least 60 years old.

10. The method of claim 1, wherein the composition is administered orally.

11. The method of claim 1, wherein the composition further comprises one or more preservatives, flavorings, colorings, stabilizers, emulsifiers, or other pharmaceutically acceptable excipients.

12. The method of claim 1, wherein the infectious disease comprises one or more symptoms comprising shortness of breath, wheezing, coughing, yellow mucus, green mucus, blood-tinged mucus, chest pain, breathlessness, rapid breathing, hypoxia, inflammation of the lung tissue, rapid heart rate, or increased blood pressure, or decreased blood pressure.

13. The method of claim 1, wherein the infectious disease comprises a bacterial infection.

14. The method of claim 13, wherein the bacterial infection comprises one or more of *Streptococcus pneumoniae*, *Mycobacterium tuberculosis*, *Bordetella pertussis*, *Haemophilus influenzae*, *Moraxella catarrhalis*, *Pseudomonas aeruginosa*, *Stenotrophomonas maltophila*, *Staphylococcus aureus*, *Streptococcus pyogenes*, *Neisseria meningitidis*, *Klebsiella pneumoniae*, or Non-tuberculosis *Mycobacterium*.

15. The method of claim 1, wherein the infectious disease comprises a viral infection.

16. The method of claim 15, wherein the viral infection comprises one or more of Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBoV), Orthomyxoviridae (influenza A, B, C, D, Isavirus, Thogotovirus, Quaranjavirus), or Herpesviridae (human herpes viruses, Varicella zoster virus, Epstein-Barr virus, cytomegalovirus).

17. The method of claim 16, wherein the CoV comprises one or more of Severe Acute Respiratory Syndrome (SARS-CoV), Middle East Respiratory Syndrome (MERS-CoV), COVID-19 (2019-nCoV, SARS-CoV-2), 229E, NL63, 0043, or HKU1.

18. The method of claim 1, wherein the symptoms of an infectious disease comprises an inflammatory response associated with a bacterial or viral infection.

19. The method of claim 1, wherein the administration modulates one or more of cytokine storms, neuroinflammation, or blood clotting.

* * * * *

SEQUENCE LISTING

```
Sequence total quantity: 13
SEQ ID NO: 1              moltype = DNA   length = 530
FEATURE                  Location/Qualifiers
source                   1..530
                         mol_type = genomic DNA
                         organism = Fomitopsis officinalis
SEQUENCE: 1
ctggccttcc gggcatgtgc acgccccact cattccaaat tctcatacac ctgtgcacat   60
cctgtakgtt tggtttgagt kgcggtctct tcgcggagat tgcggctcgg cctttcctat  120
gttatatata aactctatac agtctgcaga atgtaaaccg cgtttaacgc attaaataca  180
actttcagca acggatctct tggttctcgc atcgatgaag aacgcagcga aatgcgataa  240
gtaatgtgaa ttgcagaatt cagtgaatca tcgaatcttt gaacgcacct tgcgctcctt  300
ggtattccga ggagcatgcc tgtttgagtg tcatggaatt ctcaaccccc atcacctttg  360
ttggtggtgt gtgggcttgg atttggaggt tttctgccgg acggtcaaac gttcggctcc  420
tcttgaatgc attagcttgg acctctgtgt atcttgctca atccggtgtg atagttttgt  480
ctacgctgga gggtttacac tctgtgaggg tttgggcttc caatcgtcct             530

SEQ ID NO: 2              moltype = DNA   length = 515
FEATURE                  Location/Qualifiers
source                   1..515
```

```
                        mol_type = genomic DNA
                        organism = Fomitopsis officinalis
SEQUENCE: 2
tgtagctggc cttccgggca tgtgcacgcc ccactcattc caaattctca tacacctgtg   60
cacatcctgt aggtttggtt tgagttgcgg tctcttcgcg gagattgcgg ctcggccttt  120
cctatgttat atataaactc tatacagtct gcagaatgta aaccgcgttt aacgcattaa  180
atacaacttt cagcaacgga tctcttggtt ctcgcatcga tgaagaacgc agcgaaatgc  240
gataagtaat gtgaattgca gaattcagtg aatcatcgaa tctttgaacg caccttgcgc  300
tccttggtat tccgaggagc atgcctgttt gagtgtcatg gaattctcaa cccccatcac  360
ctttgttggt ggtgtgtggg cttggatttg gaggttttct gccggacggt caaacgttcg  420
gctcctcttg aatgcattag cttggacctc tgtgtatctt gctcaatccg gtgtgatagt  480
tttgtctacg cyggagggtt tacactctgt gaggg                            515

SEQ ID NO: 3              moltype = DNA   length = 484
FEATURE                  Location/Qualifiers
source                   1..484
                         mol_type = genomic DNA
                         organism = Fomitopsis officinalis
SEQUENCE: 3
ggcatgtgca cgccccactc attccaaatt ctcatacacc tgtgcacatc ctgtaggttt   60
ggtttgagtk gcggtctctt cgcggagatt gcggctcggc ctttcctatg ttatatatat  120
aaactctata castctgcag aatgtaaacc gcgtttaacg cattaaatac aactttcagc  180
aacggatctc ttggttctcg catcgatgaa gaacgcagcg aaatgcgata agtaatgtga  240
attgcagaat tcagtgaatc atcgaatctt tgaacgcacc ttgcgctcct ggtattccg  300
aggagcatgc ctgtttgagt gtcatggaat tctcaacccc catcacctt gttggtggtg  360
tgtgggcttg gatttggagg ttttctgccg gacggtcaaa cgttcggctc ctcttgaatg  420
cattagcttg gacctctgtg tatcttgctc aatccggtgt gatagttttg tctacgccgg  480
aggg                                                              484

SEQ ID NO: 4              moltype = DNA   length = 602
FEATURE                  Location/Qualifiers
source                   1..602
                         mol_type = genomic DNA
                         organism = Fomitopsis officinalis
SEQUENCE: 4
tgtagctggc cttccgggca tgtgcacgcc ccactcattc caaattctca tacacctgtg   60
cacatcctgt aggtttggtt tgagttgcgg tctcttcgcg gagattgcgg ctcggccttt  120
cctatgttat atataaactc tatacagtct gcagaatgta aaccgcgttt aacgcattaa  180
atacaacttt cagcaacgga tctcttggtt ctcgcatcga tgaagaacgc agcgaaatgc  240
gataagtaat gtgaattgca gaattcagtg aatcatcgaa tctttgaacg caccttgcgc  300
tccttggtat tccgaggagc atgcctgttt gagtgtcatg gaattctcaa ccccatcac  360
ctttgttggt ggtgtgtggg cttggatttg gaggttttct gccggacggt caaacgttcg  420
gctcctcttg aatgcattag cttggacctc tgtgtatctt gctcaatccg gtgtgatagt  480
tttgtctacg ctggagggtt tacactctgt gagggtttgg gcttccaatc gtcctttcgg  540
acaattgttt ttttgacctc tgacctcaaa tcaggtagga ttacccgctg aacttaagca  600
ta                                                                602

SEQ ID NO: 5              moltype = DNA   length = 450
FEATURE                  Location/Qualifiers
source                   1..450
                         mol_type = genomic DNA
                         organism = Fomitopsis officinalis
SEQUENCE: 5
cctgtgcaca tcctgtaggt ttggtttgag ttgcggtctc ttcgcggaga ttgcggctcg   60
gcctttccta tgttatatat aaactctata cagtctgcag aatgtaaacc gcgtttaacg  120
cattaaatac aactttcagc aacggatctc ttggttctcg catcgatgaa gaacgcagcg  180
aaatgcgata agtaatgtga attgcagaat tcagtgaatc atcgaatctt tgaacgcacc  240
ttgcgctcct tggtattccg aggagcatgc ctgtttgagt gtcatggaat tctcaacccc  300
catcacctt gttggtggtg tgtgggcttg gatttggagg ttttctgccg gacggtcaaa  360
cgttcggctc ctcttgaatg cattagcttg gacctctgtg tatcttgctc aatccggtgt  420
gatagttttg tctacgctgg agggtttaca                                  450

SEQ ID NO: 6              moltype = DNA   length = 704
FEATURE                  Location/Qualifiers
source                   1..704
                         mol_type = genomic DNA
                         organism = Fomitopsis officinalis
SEQUENCE: 6
ttccgtaggt gaacctgcgg aaggatcatt attgaatttt gaatggggtt gtagctggcc   60
ttccgggcat gtgcacgccc cactcattcc aaattctcat acacctgtgc acatcctgta  120
ggtttggttt gagttgcggt ctcttcgcgg agattgcggc tcggcctttc ctatgttata  180
tataaactct atacagtctg cagaatgtaa accgcgttta acgcattaaa tacaactttc  240
agcaacggat ctcttggttc tcgcatcgat gaagaacgca gcgaaatgcg ataagtaatg  300
tgaattgcag aattcagtga atcatcgaat ctttgaacgc accttgcgct ccttggtatt  360
ccgaggagca tgcctgtttg agtgtcatgg aattctcaac cccatcacc tttgttggtg  420
gtgtgtgggc ttggatttgg aggttttctg ccggacggtc aaacgttcgg ctcctcttga  480
atgcattagc ttggacctct gtgtatcttg ctcaatccgg tgtgatagtt ttgtctacgc  540
tggagggttt acactctgtg agggtttggg cttccaatcg tcctttcgga caattgtttt  600
tttgacctct gacctcaaat caggtaggat tacccgctga acttaagcat atcaataagc  660
```

-continued

```
ggaggaaaag aaactaacaa ggattcccct agtaactgcg agtg                       704

SEQ ID NO: 7          moltype = DNA   length = 672
FEATURE               Location/Qualifiers
source                1..672
                      mol_type = genomic DNA
                      organism = Fomitopsis officinalis
SEQUENCE: 7
aacaaggttt ccgtaggtga acctgcggaa ggatcattat tgaattttga atggggttgt      60
agctggcctt ccgggcatgt gcacgcccca ctcattccaa attctctac  acctgtgcac      120
atcctgtagg tttggtttga gttgcggtct cttcgcggag attgcggctc ggcctttcct      180
atgttatata taaactctat acagtctgca gaatgtaaac cgcgtttaac gcattaaata      240
caactttcag caacggatct cttggttctc gcatcgatga agaacgcagc gaaatgcgat      300
aagtaatgtg aattgcagaa ttcagtgaat catcgaatct ttgaacgcac cttgcgctcc      360
ttggtattcc gaggagcatg cctgtttgag tgtcatggaa ttctcaaccc ccatcacctt      420
tgttggtggt gtgtgggctt ggatttggag gttttctgcc ggacggtcaa acgttcggct      480
cctcttgaat gcattagctt ggacctctgt gtatcttgct caatccggtg tgatagtttt      540
gtctacgctg gagggtttac actctgtgga ggtttgggc  tccaatcgtc ctttcggaca      600
attgtttttt tgacctctga cctcaaatca ggtaggatta cccgctgaac ttaagcatat      660
caataagcgg ag                                                          672

SEQ ID NO: 8          moltype = DNA   length = 602
FEATURE               Location/Qualifiers
source                1..602
                      mol_type = genomic DNA
                      organism = Fomitopsis officinalis
SEQUENCE: 8
tgtagctggc cttccgggca tgtgcacgcc ccactcattc caaattctca tacacctgtg      60
cacatcctgt aggtttggtt tgagttgcgg tctcttcgcg gagattgcgg ctcggccttt      120
cctatgttat atataaactc tatacagtct gcagaatgta accgcgtttt aacgcattaa      180
atacaacttt cagcaacgga tctcttggtt ctcgcatcga tgaagaacgc agcgaaatgc      240
gataagtaat gtgaattgca gaattcagtg aatcatcgaa tctttgaacg caccttgcgc      300
tccttggtat tccgaggagc atgcctgttt gagtgtcatg gaattctcaa cccccatcac      360
ctttgttggt ggtgtgtggg cttggatttg gaggtttct  gccggacggt caaacgttcg      420
gctcctcttg aatgcattag cttggacctc tgtgtatctt gctcaatccg gtgtgatagt      480
tttgtctacg ctggagggtt tacactctgt gagggtttgg gcttccaatc gtcctttcgg      540
acaattgttt ttttgacctc tgacctcaaa tcaggtagga ttacccgctg aacttaagca      600
ta                                                                     602

SEQ ID NO: 9          moltype = DNA   length = 450
FEATURE               Location/Qualifiers
source                1..450
                      mol_type = genomic DNA
                      organism = Fomitopsis officinalis
SEQUENCE: 9
cctgtgcaca tcctgtaggt ttggtttgag ttgcggtctc ttcgcggaga ttgcggctcg      60
gcctttccta tgttatatat aaactctata cagtctgca  aatgtaaacc gcgtttaacg      120
cattaaatac aactttcagc aacggatctc ttggttctcg catcgatgaa gaacgcagcg      180
aaatgcgata agtaatgtga attgcagaat tcagtgaatc atcgaatctt tgaacgcacc      240
ttgcgctcct tggtattccg aggagcatgc ctgtttgagt gtcatggaat ctcaacccc      300
catcaccttt gttggtggtg tgtgggcttg gatttggagg ttttctgccg gacggtcaaa      360
cgttcggctc ctcttgaatg cattagcttg gacctctgtg tatcttgctc aatccggtgt      420
gatagttttg tctacgctgg agggtttaca                                       450

SEQ ID NO: 10         moltype = DNA   length = 579
FEATURE               Location/Qualifiers
source                1..579
                      mol_type = genomic DNA
                      organism = Fomitopsis officinalis
SEQUENCE: 10
tacacctgtg cacatcctgt aggtttggtt tgagttgcgg tctcttcgcg gagattgcgg      60
ctcggccttt cctatgttat atataaactc tatacagtct gcagaatgta aaccgcgttt      120
aacgcattaa atacaacttt cagcaacgga tctcttggtt ctcgcatcga tgaagaacgc      180
agcgaaatgc gataagtaat gtgaattgca gaattcagtg aatcatcgaa tctttgaacg      240
caccttgcgc tccttggtat tccgaggagc atgcctgttt gagtgtcatg gaattctcaa      300
ccccatcac  ctttgttggt ggtgtgtggg cttggatttg gaggtttct  gccggacggt      360
caaacgttcg gctcctcttg aatgcattag cttggacctc tgtgtatctt gctcaatccg      420
gtgtgatagt tttgtctacg ctggagggtt tacactctgt gagggtttgg gcttccaatc      480
gtcctttcgg acaattgttt ttttgacctc tgacctcaaa tcaggtagga ttacccgctg      540
aacttaagca tatcaataag cggaggaaag aaactaaca                             579

SEQ ID NO: 11         moltype = DNA   length = 528
FEATURE               Location/Qualifiers
source                1..528
                      mol_type = genomic DNA
                      organism = Fomitopsis officinalis
SEQUENCE: 11
cgccccactc attccaattc tcatacacct gtgcacatcc tgtaggtttg gtttgagttg      60
cggtctcttc gcggagattg cggctcggcc tttcctatgt tatatataaa ctctatacag      120
```

-continued

```
tctgcagaat gtaaaccgcg tttaacgcat taaatacaac tttcagcaac ggatctcttg    180
gttctcgcat cgatgaagaa cgcagcgaaa tgcgataagt aatgtgaatt gcagaattca    240
gtgaatcatc gaatctttga acgcaccttg cgctccttgg tattccgagg agcatgcctg    300
tttgagtgtc atggaattct caacccccat cacctttgtt ggtggtgtgt gggcttggat    360
ttggaggttt tctgccggac ggtcaaacgt tcggctcctc ttgaatgcat tagcttggac    420
ctctgtgtat cttgctcaat ccggtgtgat agttttgtct acgctggagg gtttacactc    480
tgtgagggtt tgggcttcca atcgtccttt cggacaattg tttttttg                 528

SEQ ID NO: 12          moltype = DNA  length = 543
FEATURE                Location/Qualifiers
source                 1..543
                       mol_type = genomic DNA
                       organism = Fomitopsis officinalis
SEQUENCE: 12
taagcatatc aataagcgga ggaaaagaaa ctaacaagga ttcccctagt aactgcgagt    60
gaagcgggaa gagctcaaat ttaaaatctg gcggtctctg gccgtccgag ttgtagtctg    120
gagaagtgct ttccgcgctg gaccgtgtac aagtcccttg gaacagggcg tcatagaggg    180
tgagaatccc gtctttgaca cggactacca gtgctttgtg atgcgctctc aaagagtcga    240
gttgtttggg aatgcagctc aaaatgggtg gtaaattcca tctaaagcta aatattggcg    300
agagaccgat agcgaacaag taccgtgagg gaaagatgaa aagcactttg gaaagagagt    360
taaacagtac gtgaaattgc tgaaagggaa acacttgaag tcagtcgcgt cggccagaac    420
tcagccttgc tcttttgctc ggtgcacttt ctggttgacg ggccagcatc gattttgacc    480
gttggataaa ggttgggggga atgtggcacc ttcgggtgtg tttatagccc tcggtcacat    540
aca                                                                   543

SEQ ID NO: 13          moltype = DNA  length = 539
FEATURE                Location/Qualifiers
source                 1..539
                       mol_type = genomic DNA
                       organism = Fomitopsis officinalis
SEQUENCE: 13
catatcaata agcggaggaa aagaaactaa caaggattcc cctagtaact gcgagtgaag    60
cgggaagagc tcaaatttaa aatctggcgg tctctggccg tccgagttgt agtctggaga    120
agtgctttcc gcgctggacc gtgtacaagt cccttggaac agggcgtcat agagggtgag    180
aatcccgtct ttgacacgga ctaccagtgc tttgtgatgc gctctcaaag agtcgagttg    240
tttgggaatg cagctcaaaa tgggtggtaa attccatcta aagctaaata ttggcgagag    300
accgatagcg aacaagtacc gtgagggaaa gatgaaaagc actttggaaa gagagttaaa    360
cagtacgtga aattgctgaa agggaaacac ttgaagtcag tcgcgtcggc cagaactcag    420
ccttgctctt ttgctcggtg cactttctgg ttgacgggcc agcatcgatt ttgaccgttg    480
gataaaggtt ggggggaatgt ggcaccttcg ggtgtgttta tagccctcgg tcacataca    539
```